(12) United States Patent
Robison et al.

(10) Patent No.: US 12,329,661 B2
(45) Date of Patent: *Jun. 17, 2025

(54) MACHINE-LEARNED MOVEMENT DETERMINATION BASED ON INTENT IDENTIFICATION

(71) Applicant: Cionic, Inc., San Francisco, CA (US)

(72) Inventors: Jeremiah Robison, San Francisco, CA (US); Michael Dean Achelis, Walnut Creek, CA (US); Lina Avancini Colucci, Los Altos, CA (US); Sidney Rafael Primas, Los Altos, CA (US); Andrew James Weitz, Bishop, CA (US)

(73) Assignee: Cionic, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/602,923

(22) Filed: Mar. 12, 2024

(65) Prior Publication Data
US 2024/0216152 A1 Jul. 4, 2024

Related U.S. Application Data

(63) Continuation of application No. 17/113,058, filed on Dec. 6, 2020, now Pat. No. 11,957,605.

(51) Int. Cl.
*A61F 2/58* (2006.01)
*G06F 3/01* (2006.01)
(Continued)

(52) U.S. Cl.
CPC .............. *A61F 2/583* (2013.01); *G06F 3/015* (2013.01); *G06F 3/016* (2013.01); *G06F 3/0346* (2013.01); *G06N 20/00* (2019.01)

(58) Field of Classification Search
None
See application file for complete search history.

(56) References Cited

U.S. PATENT DOCUMENTS 9,936,900 B2   4/2018  Chang et al.
10,086,196 B2  10/2018  Glukhovsky et al.
(Continued)

OTHER PUBLICATIONS

Bellman, M. J. et al., "Switched Control of Cadence During Stationary Cycling Induced by Functional Electrical Stimulation," IEEE Transactions on Neural Systems and Rehabilitation Engineering, Dec. 2016, pp. 1373-1383, vol. 24, No. 12.
(Continued)

*Primary Examiner* — Toan H Vu
(74) *Attorney, Agent, or Firm* — Fenwick & West LLP

(57) ABSTRACT

A mobility augmentation system monitors data representative of a user's motor intent and augments the user's mobility based on the monitored motor intent data. A machine-learned model is trained to identify an intended movement based on the monitored motor intent data. The machine-learned model may be trained based on generalized or specific motor intent data (e.g., user-specific motor intent data). A machine-learned model initially trained on generalized motor intent data may be re-trained on user-specific motor intent data such that the machine-learned model is optimized to the movements of the user. The system uses the machine-learned model to identify a difference between the user's monitored movement and target movement signals. Based on the identified difference, the system determines actuation signals to augment the user's movement. The actuation signals determined can be an adjustment to a currently applied actuation such that the system optimizes the actuation strategy during application.

20 Claims, 13 Drawing Sheets

(51) Int. Cl.
*G06F 3/0346* (2013.01)
*G06N 20/00* (2019.01)

(56) References Cited

U.S. PATENT DOCUMENTS

| | | | |
|---|---|---|---|
| 10,657,656 B2* | 5/2020 | Cavallo | G06N 20/00 |
| 10,854,104 B2 | 12/2020 | Mettler May | |
| 11,614,796 B1 | 3/2023 | Summit | |
| 11,747,806 B1* | 9/2023 | Wootton | G08G 1/161 |
| | | | 701/28 |
| 11,772,259 B1 | 10/2023 | Kiehl et al. | |
| 2011/0112996 A1 | 5/2011 | Tu et al. | |
| 2013/0208127 A1 | 8/2013 | Chou et al. | |
| 2014/0184849 A1 | 7/2014 | Kim | |
| 2014/0354845 A1 | 12/2014 | Mølgaard et al. | |
| 2016/0103487 A1 | 4/2016 | Crawford et al. | |
| 2017/0057497 A1 | 3/2017 | Laur et al. | |
| 2017/0236073 A1 | 8/2017 | Borisyuk et al. | |
| 2019/0009133 A1 | 1/2019 | Mettler May | |
| 2019/0038222 A1 | 2/2019 | Krimon et al. | |
| 2021/0254979 A1 | 8/2021 | Faragher et al. | |
| 2021/0256872 A1 | 8/2021 | Matsumoto et al. | |
| 2021/0326583 A1 | 10/2021 | Donatsch et al. | |
| 2022/0080545 A1* | 3/2022 | Sanders | B23Q 17/20 |
| 2022/0269346 A1 | 8/2022 | Hussami et al. | |
| 2022/0395041 A1* | 12/2022 | Witchey | A61B 5/6803 |

OTHER PUBLICATIONS

Bioness Inc., "The L300 Foot Drop System," undated, one page, [Online] [Retrieved on Jan. 5, 2021], Retrieved from the Internet <URL: https://www.bioness.com/Products/L300_for_foot_drop.php>.

Buchanan, T. S. et al., "Estimation of Muscle Forces and Joint Moments Using a Forward-Inverse Dynamics Model," Medicine & Science in Sports & Exercise, Nov. 2005, pp. 1911-1916, vol. 37, No. 11.

Cauraugh, J. et al., "Chronic Motor Dysfunction After Stroke, Recovering Wrist and Finger Extension by Electromyography-Triggered Neuromuscular Stimulation," Stroke, Jun. 1, 2000, pp. 1360-1364, vol. 31, No. 6.

Cavanagh, P. R. et al., "Electromechanical Delay in Human Skeletal Muscle Under Concentric and Eccentric Contractions," European Journal of Applied Physiology and Occupational Physiology, 1979, pp. 159-163, vol. 42.

Esnouf, J. E. et al., "Impact on activities of daily living using a functional electrical stimulation device to improve dropped foot in people with multiple sclerosis, measured by the Canadian Occupational Performance Measure," Multiple Sclerosis, 2010, pp. 1141-1147, vol. 16, No. 9.

Mann, G. E. et al., "A Pilot Study to Investigate the Feasibility of Electrical Stimulation to Assist Gait in Parkinson's Disease," Neuromodulation: Technology at the Neural Interface, 2008, pp. 143-149, vol. 11, No. 2.

Myolyn, LLC, "Myocycle Fes Therapy System," undated, six pages, [Online] [Retrieved on Jan. 6, 2021], Retrieved from the Internet <URL: https://myolyn.com>.

Naghavi, N. et al., "Prediction of Freezing of Gait in Parkinson's Disease Using Statistical Inference and Lower-Limb Acceleration Data," IEEE Transactions on Neural Systems and Rehabilitation Engineering, May 2019, pp. 947-955, vol. 27, No. 5.

Odstock Medical Ltd (OML)., "Stimulators," undated, one page, [Online] [Retrieved on Jan. 5, 2021], Retrieved from the Internet <URL: https://www.odstockmedical.com/products/stimulators>.

PCT International Search Report and Written Opinion, PCT Application No. PCT/US2021/061449, Apr. 8, 2022, 15 pages.

PCT Invitation to Pay Additional Fees, PCT Application No. PCT/US2021/61449, Feb. 14, 2022, two pages.

Pelicioni, P. H. S. et al., "Falls in Parkinson's Disease Subtypes: Risk Factors, Locations and Circumstances," International Journal of Environmental Research and Public Health, 2019, nine pages, vol. 16, No. 12.

Piyus, C. K. et al., "EMG based FES for post-stroke rehabilitation," IOP Conf. Series: Materials and Engineering, 2017, seven pages, vol. 263, No. 052025.

Popa, L. et al., "Functional electrical stimulation may reduce bradykinesia in Parkinson's disease: a Feasibility study," Journal of Rehabilitation and Assistive Technologies Engineering, Oct. 26, 2015, eight pages.

Pulliam, C. L. et al., "Continuous Assessment of Levodopa Response in Parkinson's Disease Using Wearable Motion Sensors," IEEE Transactions on Biomedical Engineering, Jan. 2018, pp. 159-164, vol. 65, No. 1.

Taylor, P. N. et al., "Clinical Use of the Odstock Dropped Foot Stimulator: Its Effect on the Speed and Effort of Walking," Arch Phys Med Rehabil, Dec. 1999, pp. 1577-1583, vol. 80.

Office Action, U.S. Appl. No. 17/113,059, filed Nov. 9, 2023, 21 pages.

Wille C. M. et al., "Ability of Sagittal Kinematic Variables to Estimate Ground Reaction Forces and Joint Kinetics in Running," Journal of Orthopaedic & Sports Physical Therapy, Oct. 2014, pp. 825-830, vol. 44, No. 10.

Wouda, F. J. et al., "Estimation of Vertical Ground Reaction Forces and Sagittal Knee Kinematics During Running Using Three Inertial Sensors," Frontiers in Physiology, Mar. 2018, 14 pages, vol. 9, No. 218.

Yeom, H. et al., "Autogenic EMG-controlled functional electrical stimulation for ankle dorsiflexion control," Journal of Neuroscience Methods, 2010, pp. 118-125, vol. 193.

Zhan, A. et al., "High Frequency Remote Monitoring of Parkinson's Disease via Smartphone: Platform Overview and Medication Response Detection," arXiv:1601.00960v1, Jan. 5, 2016, 12 pages.

European Patent Office, Extended European Search Report and Opinion, EP Patent Application No. 21901407.3, Oct. 11, 2024, seven pages.

Office Action, U.S. Appl. No. 18/653,767, filed Nov. 21, 2024, 16 pages.

\* cited by examiner

MACHINE-LEARNED MOVEMENT DETERMINATION BASED ON INTENT IDENTIFICATION

CROSS REFERENCE TO RELATED APPLICATIONS

This application is a continuation of U.S. application Ser. No. 17/113,058, filed Dec. 6, 2020, now U.S. Pat. No. 11,957,605, which is incorporated by reference in its entirety. This application is also related to U.S. application Ser. No. 17/113,059, filed Dec. 6, 2020, now U.S. Pat. No. 12,005,573, which is incorporated by reference in its entirety.

TECHNICAL FIELD

This disclosure relates generally to a mobility augmentation system, and more specifically to using movement intent to optimize and personalize mobility augmentation.

BACKGROUND

Hundreds of millions of people live with a disability. In the United States, approximately 14% of adults with a disability have a mobility disability that causes a person serious difficulty walking or climbing stairs, according to a 2019 study by the Centers for Disease Control and Prevention. Conventional methods of assisting mobility, such as crutches, canes, and wheelchairs are not sufficient to enable individuals to achieve full independence and mobility.

While technology such as exoskeletons and therapeutics such as functional electrical stimulation (FES) mark improvements over conventional methods for increasing mobility, such technology suffers from similar limitations as conventional crutches, canes, and wheelchairs: they are not personalized to the user and fail to optimize mobility augmentation based on available information (e.g., the user's movement). Accordingly, existing technology may be improved by personalizing and optimizing mobility augmentation.

SUMMARY

The mobility augmentation system described herein implements machine learning and control mechanisms to personalize and optimize mobility augmentation. The system monitors the user for various data associated with movement such as muscle electroactivity (i.e., muscle firing), kinematics, and kinetics. By monitoring muscle electroactivity, the system can determine what movement the user intends to make before the user makes it. This is an improvement over conventional systems that merely use inertial measurement unit (IMU) data indicative of a user's current movement to determine whether to augment movement. This reactive approach taken by conventional systems cannot assist users impacted with neuro-atypical motor function before they attempt a neurotypical movement.

The mobility augmentation system described herein determines intended movements using a machine-learned model that identifies an intended movement or movement prediction based on monitored data such as muscle electroactivity, kinematics, and kinetics. The machine-learned model can be trained on generalized movement data collected across a population of users or on data associated with a particular user's movement, which fine tunes its movement predictions for that user and enables personalized mobility augmentation. The system uses the movement prediction to determine mobility augmentation or an actuation strategy. This actuation strategy can be further personalized to a user.

Once the system applies an actuation strategy, it further monitors the user's movement to gauge how successful the applied actuation strategy was. By comparing the monitored movement and target movement associated with the user's intention, the system can re-train the machine-learned model (e.g., when the actuation strategy was appropriate for the identified intended movement). In this way, the system further personalizes the mobility augmentation to the user. Furthermore, after comparing the monitored and target movements, the system may adjust the actuation strategy to minimize subsequent differences between monitored and target movements. Accordingly, the system optimizes actuation strategies by monitoring the user after applying actuation.

In one embodiment, the mobility augmentation system collects a first set of motor intent data of one or more users from a database. Examples of motor intent data include electromyography (EMG) data, IMU data, foot plantar pressure signals, or a combination thereof. The system labels the first set of motor intent data with an intent label representative of intended motion characterized by the first set of motor intent data. For example, the motor intent data may be labeled with an intent label that indicates that a user intended to take a step forward or lift a toe. The system creates, based on the labeled first set of motor data, a first training set to train a machine learning model. The machine learning model is configured to output, based on monitored motor intent data, a movement prediction corresponding to likely motion characterized by the monitored motor intent data. The monitored motor intent data may be captured by sensors located at various areas on a user's body (e.g., a target user distinct from the users that contributed to the first set of motor intent data). The system creates a second training set based on the movement prediction and a second set of motor intent data corresponding to movement signals of the target user. The machine learning model is re-trained using the second training set such that it is customized to the motions of the target user.

In another embodiment, the mobility augmentation system applies a machine learning model to identify an intended movement of a user. The system monitors movement signals representative of the user's movement. The machine learning model is used to determine an intended movement of the user based on motor intent data received from the user (e.g., via sensors located on the user's body). Using the intended movement determination, the system identifies a difference between the movement signals and target movement signals. The target movement signals may be representative of the user's intended movement. For example, the system determines that the user intends to stand up, and the target movement signals include kinematic, kinetic, EMG signals, or any combination thereof associated with neurotypical standing movement. The system determines actuation signals based on this identified difference between monitored and target movement signals. For example, parameters for an FES stimulation for assisting a user in standing may be determined based on how close the user's monitored movement is to the target movement. The system then applies the determined actuation signals to one or more augmentation devices, or "mobility augmentation devices," worn by the user. For example, the determined FES stimulation may be applied through actuation electrodes located at each of the devices.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

System Architecture

Figure 1:
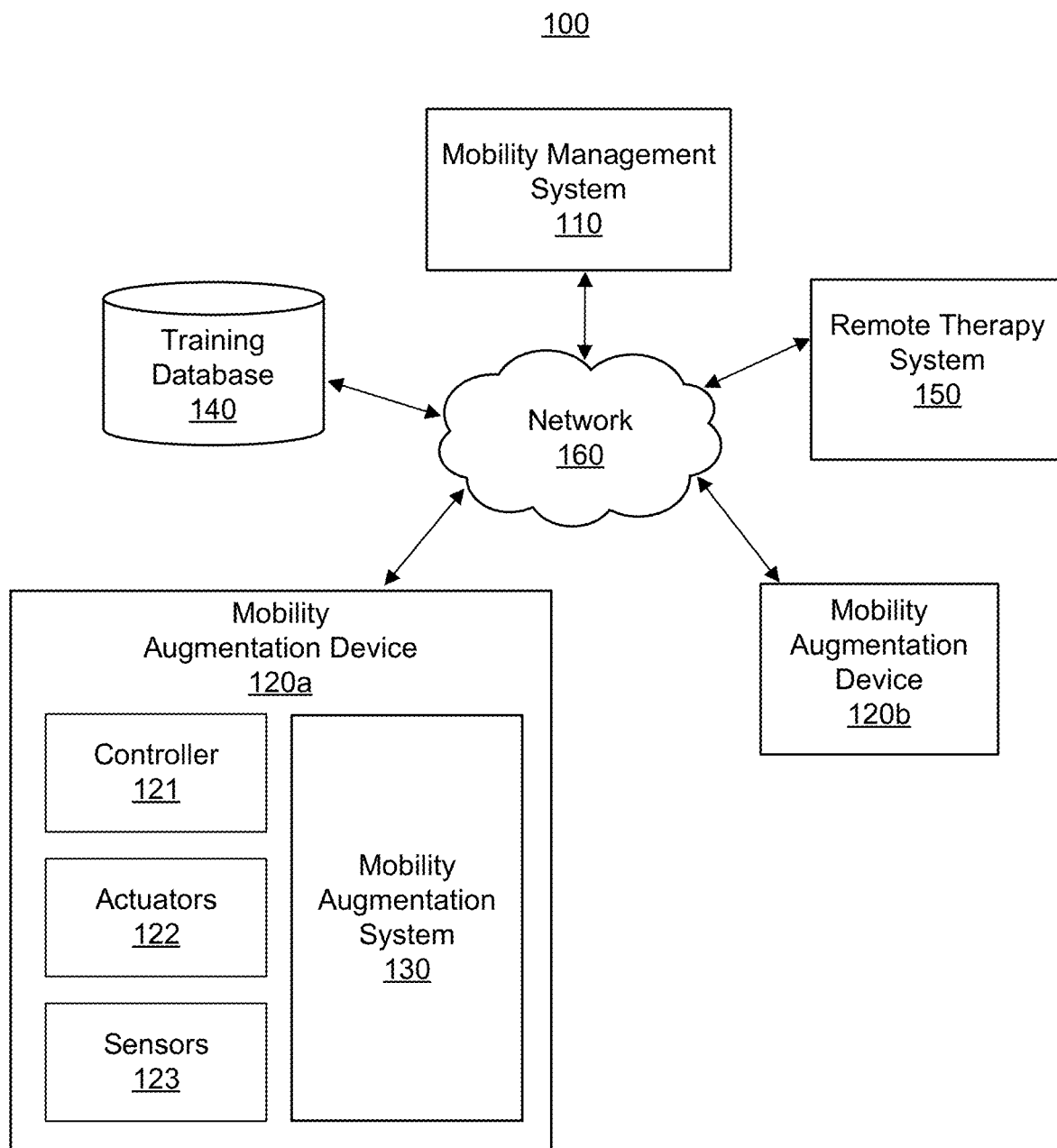
FIG. 1 is a block diagram of a system environment in which a mobility augmentation device operates, in accordance with at least one embodiment.

FIG. 1 is a block diagram of a system environment 100 in which mobility augmentation devices operate. The system environment 100 shown by FIG. 1 includes a mobility management system 110, mobility augmentation devices 120a and 120b, a mobility augmentation system 130, a training database 140, a remote therapy system 150, and a network 160. The system environment 100 may have alternative configurations than shown in FIG. 1, including for example different, fewer, or additional components. For example, an additional mobility augmentation device may be communicatively coupled with the network 160 to the mobility management system 110. In another example, the remote therapy system 150 may be omitted from the system environment 100 without compromising the functionality of the mobility augmentation devices 120a and 120b.

The system environment 100 enables the augmentation devices 120a and 120b to increase the mobility of its users. In a first example, a child with Cerebral palsy wears the mobility augmentation devices 120a and 120b at different locations on his body to step more naturally through his gait. In a second example, a patient suffering from advanced Parkinson's Disease (e.g., experiencing motor symptoms including tremors and freezing) wears one or more of the mobility augmentation devices 120a and 120b to restore his ability to perform otherwise difficult activities (e.g., standing up from a chair).

While the previous examples involved users with neuroatypical movement, the system environment 100 may also help users with neurotypical movement increase or maintain their mobility. In a third example, a first responder carrying an injured person from a wreckage site wears the mobility augmentation device 120a to maintain her stamina or increase her speed to save lives. In a fourth example, a dancer wears the mobility augmentation device 120a to improve her form while performing an arabesque. In some embodiments, the system environment 100 may assist medical professionals in diagnosing or treating their patients. In a fifth example, a clinician wears the mobility augmentation device 120a to experience the muscle stimulation the device 120a delivers to the clinician's patient. This fifth example may improve a clinician's understanding of what the patient's muscle sequencing is like (e.g., during an educational course, physical training, or therapy) as compared to the patient try to explain what the patient's muscle sequencing feels like during movement.

The mobility augmentation devices 120a and 120b increase the mobility of its users by monitoring for a user's intended movement and modifying or augmenting the movement by applying actuation signals. The devices 120a and 120b may determine the actuation signals using target movement signals (e.g., neurotypical movement). The devices 120a and 120b may be worn at various locations on the body of the user to monitor for the user's intended movement or motor intent data. For example, the devices 120a and 120b may use electromyography to monitor the electrical activity of the user's muscles. From the monitored electrical activity, the devices 120a and 120b may determine the user's intended movement using one or more machine learning models trained to identify a likely movement the user intends to make. The devices 120a and 120b may determine actuation signals to apply based on the identified intention. After the devices 120a and 120b determine the actuation signals to apply, the devices 120a and 120b apply the actuation signals to the various locations on the body of the user.

The mobility augmentation devices 120a and 120b enable both personalization and optimization of mobility augmentation for their users. One way in which the devices 120a and 120b personalize mobility augmentation is by using movement data collected from a given user's movement history to train a user-specific machine learning model that is used in determining the actuation signals for augmenting the user's subsequent movements. The devices 120a and 120b may optimize mobility augmentation by measuring the success of the actuation signals in real time and varying the subsequently applied actuation signals based on the measurement. Another way that the devices 120a and 120b optimize mobility augmentation may be through initial and continuous electric or electronic calibrations before and during collection of a user's movement signals used for determining the user's intended movement. Personalization and optimization will be described in further detail throughout the description of the mobility augmentation system 130 in FIG. 2.

As referred to herein, a "movement signal" is a signal representative of a user's movement. For example, the movement signal may be a kinematic, kinetic, foot pressure, or electrical activity signal, or any suitable combination thereof. Movement data may be a collection of one or more movement signals. As referred to herein, "motor intent data" is data representing a user's intended movement before or during the movement. For example, electrical activity of a user's muscle monitored by the mobility augmentation device 120a via electromyography represents the user's intention to take a step backwards before he takes the step. As referred to herein, a "target movement signal" is a signal representative of desired movement. For example, kinematic signals collected across a population with neurotypical gaits may be averaged to create a target movement signal for a gait.

As referred to herein, an "actuation signal" is a signal carrying stimulation or instructions to actuate stimulation. For example, an actuation signal can be an FES signal applied via an electrode or instructions to reverse contraction motors of a prosthetic hand. An actuation strategy may be a particular delivery of one or more actuation signals to one or more portions of a user's body to achieve a target movement signal. The terms "movement" and "motion" maybe used interchangeably herein to refer to a body's change in position over time. The terms "target user" and "user" maybe used interchangeably herein to refer to a wearer of a mobility augmentation device unless another meaning is apparent from the context. Although "users" described herein are human users, the systems and methods described herein may be similarly applied to augmenting movement for animals as well.

The mobility management system 110 monitors and processes data from the mobility augmentation devices 120a and 120b. The data received from the devices 120a and 120b may include motor intent data, movement data, and applied actuation strategies. This data may be used to generate new actuation strategies or modify existing actuation strategies. The mobility management system 110 may provide actuation strategies to the augmentation devices 120a and 120b. For example, during initial use and if the augmentation device 120a has not already been customized to its user, the mobility management system 110 may provide an actuation strategy with target movement signals representative of a neurotypical gait that has been generalized from the neurotypical gaits of a group of people. The mobility management system 110 may be hosted on a server or computing device (e.g., a smartphone) that communicates with the mobility augmentation devices 120a and 120b via the network 160.

In some embodiments, the mobility management system 110 trains and applies one or more machine learning models configured to determine a user's intended movement based on monitored motor intent data. The mobility management system 110 may maintain machine learning models in addition to or alternative to the mobility augmentation devices 120a and 120b maintaining the models. In one embodiment, the mobility management system 110 trains the models based on motor intent data collected by the devices 120a and 120b. The devices 120a and 120b send, via the network 160, motor intent data to the mobility management system 110 and leverage the trained machine learning models to receive, from the mobility management system 110, a likely intended movement determined by the one or more models. The mobility management system 110 may maintain models that are generalized to movement across a population or customized to a particular user, movement type, any suitable phenotypic trait, or a combination thereof. The training and application of machine learning models used for augmenting mobility is further described in the description of FIG. 2.

Mobility augmentation devices 120a and 120b augment a user's movement by monitoring intended movement data and applying actuation signals determined based on a target movement signal. The devices 120a and 120b may optimize the augmented movement by implementing a control system that adjusts the applied actuation signals over time to minimize a difference between the target movement signal and monitored movement signals. The device 120a includes a controller 121, actuators 122, sensors 123, and a mobility augmentation system 130. The device 120b includes similar hardware and software components as in the device 120a.

The devices 120a and 120b may have alternative configurations than shown in FIG. 1, including for example different, fewer, or additional components. For example, the devices 120a and 120b may include additional components such as one or more processors (e.g., a general purpose processor and digital signal processor), wireless communications circuitry for enabling communication via the network 160, signal generators for generating functional electrical stimulation, an input interface (e.g., a keyboard or a microphone), an output interface (e.g., a speaker or a display), supplemental memory (e.g., an SD memory card), or a power source. Additionally, although the controller 121 is depicted as separate from the mobility augmentation system 130, the mobility augmentation system 130 may perform the functionality of the controller 121 (i.e., the controller 121 is encompassed within the system 130).

The mobility augmentation devices 120a and 120b may have various, wearable form factors such as exoskeletons, modular electrode straps, leggings, foot pressure beds, any wearable form factor suitable for targeting a particular muscle group on a user's body, or a combination thereof. For example, the device 120a may be a legging that is worn underneath regular attire and is equipped with the sensors 123 and actuators 122 for performing the mobility augmentation described herein. Examples of form factors are illustrated in and further described in the descriptions of FIGS. 7-9.

The controller 121 optimizes the actuation strategy implemented by the mobility augmentation device 120a to minimize the difference between a target movement signal and a measured movement signal. In some embodiments, the sensors 123 measure the user's movement while the actuation strategy is applied by the actuators 122. The controller 121 compares the measured movement signals to target movement signals. Based on the comparison, the controller 121 modifies the actuation strategy. A feedback process implemented by controller 121 is described in further detail in the description of FIG. 3.

The actuators 122 apply actuation signals to the user. The actuators 122 may have varying types including electric, mechanic, haptic, audio, visual, pneumatic, hydraulic, or any combination thereof. The form factor of the mobility augmentation devices 120a and 120b may determine the type of the actuators 122. For example, a mobility augmentation device having an exoskeleton form factor may include a combination of pneumatic and hydraulic actuators, where applying an actuation signal involves actuating a limb of the exoskeleton via one of the pneumatic and hydraulic actuators. The mobility augmentation system 130 may determine the combination of actuation types to use depending on the user such that the mobility augmentation is personalized to the user. For example, the mobility augmentation system 130 may determine that the user's gait is maximally optimized when haptic actuation is applied instead of visual or audio actuation by monitoring the user's augmented movement and determining associations between augmented movement and the actuation type.

The actuation signals may be determined by the mobility augmentation system 130 or manually specified by an operator (e.g., a physical therapist) or the user through an input interface on the devices 120a and 120b. In some embodiments, the actuation signal is an FES signal characterized by a frequency, a pulse duration, and an amplitude (e.g., a value of current in milliamperes). The mobility augmentation system 130 may determine if and how the actuation signal changes over time. For example, the FES signal may have a first frequency, a first pulse duration, and a first amplitude for a first period of time, and then a second frequency, a second pulse duration, and a second amplitude for a second period of time following the first period of time.

The actuators 122 may execute a variety of actuation types. Examples of actuation types include manually triggered actuation, amplification, contralateral replay, body-to-body coaching, templated sequencing, and responsive optimization. The user of the mobility augmentation device 120a or a third party may manually trigger an actuation via the actuators 122. For example, a user can instruct the device 120a to generate FES stimulation and apply via the actuators 122). Other actuation types may be automatically determined by the mobility augmentation devices 120a or 120b, and are described both in the following paragraphs and in the description of FIGS. 2-3.

During amplification, the actuators 122 amplify a user's existing movements. For example, the actuators 122 use FES to stimulate muscles involved in closing a fist as the user is closing his fist to grasp an object. In contrast, amplification may not be applicable to a user with tremors due to Parkinson's Disease, as amplification would worsen his condition. Amplification may be accomplished by sensing electroactivity from a particular muscle and subsequently triggering FES in the same muscle. In some embodiments, amplification is used to calibrate sensor position and the intensity of stimulation. Calibration is further described in the description of FIG. 2.

Contralateral replay may be applicable for users who have an injury or weakness on one side of their body and not the other (e.g., users who have suffered from a stroke). The mobility augmentation devices 120a and 120b may enable a user to leverage the user's stronger side of their body to help train the movements of the weaker side. The device 120a may be located at a first location on the user's body and the device 120b is located at a second location that is mirrored across the sagittal plane of the user's body. For example, the sensors 123 located on both the left and right leg may be used to monitor the user's motor intent data and movement data, while the actuators 122 on the weaker, right leg are used to apply the actuation. The sensors 123 capture the muscle firing or kinematic patterns from the left leg and the mobility augmentation system 130 determines, based on these patterns from the left leg, the actuation to apply via the actuators 122 on the right leg.

Body-to-body coaching involves the participation of an operator or third-party user to produce target movement signals to coach the user wearing the mobility augmentation devices 120a and 120b. In some embodiments, the operator is equipped with a mobility augmentation device having sensors to measure the operator's movement or intended movement prior to movement (e.g., EMG signals). The operator's mobility augmentation device provides the measured data or identified movement associated with the measured data over the network 160 for the devices 120a or 120b to receive. For example, the operator's mobility augmentation device may send data collected from IMU sensors or may process the data to determine the operator is lifting his right foot and send that determination to the devices 120a or 120b. The devices 120a or 120b may then reproduce the operator's motion on the user. For example, the devices 120a receives the indication that the operator lifted his right foot and the mobility augmentation system 130 determines the appropriate actuation strategy to lift the user's right foot.

The actuators 122 may implement templated sequencing, applying actuation signals based on templates associated with particular movements. The mobility management system 110 may collect data across neurotypical populations to form the templates. In some embodiments, the templates include a sequence of mappings between specific events in a movement that corresponds to the beginning of ending of a specific muscle firing. The sequence of mappings are organized chronologically in the order in which the events occur in a movement. For example, a template for a gait can include events associated with a foot leaving the ground followed by events associated with a leg lift, swing, and finally, the heel of the foot striking the ground to complete the gait. An example visualization of a template is described in the description of FIG. 4.

Responsive optimization may be performed in addition to any one of the aforementioned actuation types. In particular, the mobility augmentation devices 120a and 120b can gauge the success of the actuation strategy applied by the actuators 122 and adjust subsequent actuation to minimize the difference between target and measured movement. The adjusted actuation is then applied by the actuators 122. Responsive optimization is further described in the description of FIG. 2.

The sensors 123 monitor the user for intended movement data and movement data. The sensors 123 may be one or more of a microelectromechanical systems (MEMS) device, IMU, sensing electrodes, pressure sensor bed, any suitable device for measuring kinetic or electrical signals produced by a muscle, or a combination thereof. The sensors 123 may be located at various locations on the user's body. For example, a pressure sensor bed may be placed in the user's right shoe to measure the user's right foot pressure as he completes a gait. A set of sensing electrodes may be placed at the shank of the user's right leg to measure the intended movement data before and during the gait. The sensors 123 may be communicatively coupled to the controller 121 or a processor of the mobility augmentation device 120a to provide the monitored data to determine or optimize actuation signals applied by the actuators 122.

The mobility augmentation system 130 determines an intended movement of the user and augments the movement associated with the user's intention. In some embodiments, the mobility augmentation system 130 receives intended movement data from the sensors 123 and preprocesses the data before applying one or more machine learning models to the preprocessed intended movement data. The one or more machine learning models are configured to determine the user's intended movement such as standing up or stepping forward. Once the intended movement is determined, the mobility augmentation system 130 determines a difference between the user's current movement and the intended movement. The mobility augmentation system 130 may determine this difference by identifying target movement signals representative of the intended movement and comparing the target movement signals to movement signals included in the movement data received from the sensors 123. The mobility augmentation system 130 determines actuation signals to apply based on the determined difference. For example, the mobility augmentation system 130 may determine the amplitude of FES to the user's legs as proportional to the difference between a movement signal and a target movement signal (i.e., the smaller the error, the less stimulation needed to augment the user's movement to achieve the desired movement). The mobility augmentation system 130 is further described in the description of FIG. 2.

The training database 140 includes various data for training machine learning models of the mobility augmentation system 130. The data stored in the training database 140 may include labeled or unlabeled motor intent data and associated movement data (i.e., the measured movement associated with the intention), labels associated with movements, or templates associated with sequences of muscle firings for given movements. The mobility management system 110 or the mobility augmentation devices 120a and 120b may access the stored data to train machine learning models. The mobility augmentation devices 120a and 120b may provide their measured data to the training database 140. The provided data may be organized in a data structure including the measured data, biographical information identifying the user and phenotypic traits, and a label identifying the intended movement.

The remote therapy system 150 enables a third party (e.g., a medical professional or athletic coach) to monitor the user's movement and analyze the information to further augment the user's movement. For example, a physician uses the remote therapy system 150 to monitor his patient's movement and adjust an actuation strategy upon identifying that the patient's movement is not improving under the current actuation strategy. In particular, the electrical activity data of a patient's muscles measured by mobility augmentation devices 120a and 120b help a physician diagnose the needs of the patient more accurately than related systems of art that rely solely upon IMU data to trigger movement augmentation. The remote therapy system 150 may be a software module that the third party may execute on a computing device (e.g., a smartphone). In some embodiments, the remote therapy system 150 is a standalone device that may be communicatively coupled to a mobility augmentation device to manually adjust or generate actuation signals used to augment the user's motion (e.g., overriding the mobility augmentation system 130). The remote therapy system 150 may include an input interface for the third party to specify parameters of an actuation signal (e.g., the amplitude and frequency of FES signals) and when to apply them.

The remote therapy system 150 may provide actuation strategies to be applied by the mobility augmentation system 130. In some embodiments, a user of the remote therapy system 150 (e.g., a therapist) may specify when to apply stimulation and, for an array of mobility augmentation devices worn by a patient, which of the devices to apply stimulation to. For example, the therapist may define where and when to stimulate the patient's gait based on a video camera of the sensors 123 that capture the patient's gait. The therapist-specified actuation strategy may be communicated from the remote therapy system 150 to the mobility augmentation devices 120a and 120b over the network 160.

The network 160 may serve to communicatively couple the mobility management system 110, the mobility augmentation devices 120a and 120b, the training database 140, and the remote therapy system 150. For example, the mobility augmentation device 120a and the remote therapy system 150 are configured to communicate via the network 160. In some embodiments, the network 160 includes any combination of local area and/or wide area networks, using wired and/or wireless communication systems. The network 160 may use standard communications technologies and/or protocols. For example, the network 160 includes communication links using technologies such as Ethernet, 802.11, worldwide interoperability for microwave access (WiMAX), 3G, 4G, 5G, code division multiple access (CDMA), digital subscriber line (DSL), etc. Examples of networking protocols used for communicating via the network 160 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over the network may be represented using any suitable format, such as hypertext markup language (HTML) or extensible markup language (XML). In some embodiments, all or some of the communication links of the network 160 may be encrypted using any suitable technique or techniques.

Although the components of the system environment 100 are shown as connected over the network 160, one or more components may function without being connected to the network 160. For example, the augmentation devices 120a and 120b may function offline when the devices 120a and 120b are not able to connect to the network 160. When the devices 120a and 120b are able to reconnect to the network 160, they may upload monitored data or actuation results to the mobility management system 110 or the remote therapy system 150 via the network 160.

Mobility Augmentation System

Figure 2:
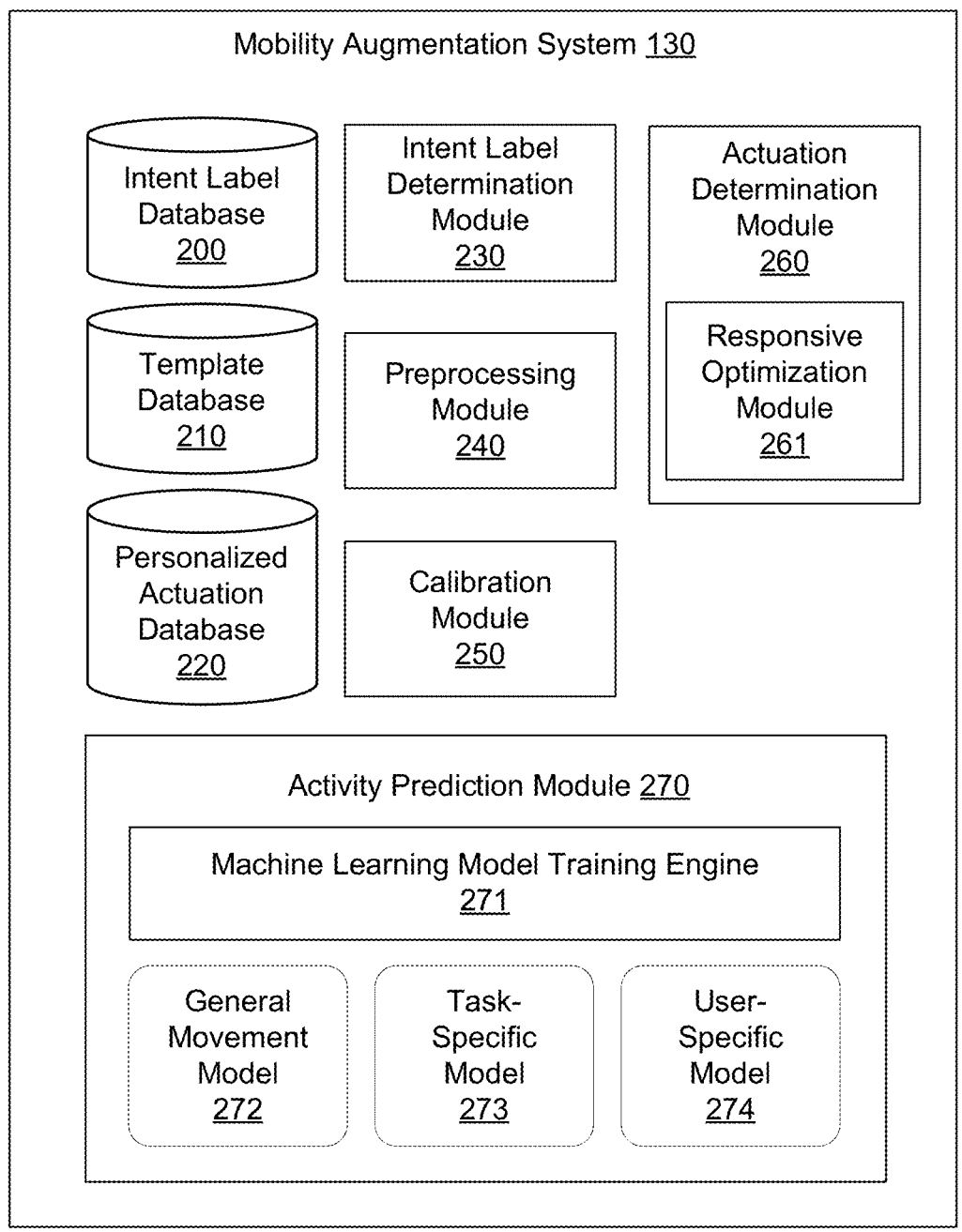
FIG. 2 is a block diagram of the mobility augmentation system of FIG. 1, in accordance with at least one embodiment.

FIG. 2 is a block diagram of the mobility augmentation system 130 of FIG. 1. The mobility augmentation system 130 includes local databases such as an intent label database 200, a template database 210, and a personalized actuation database 220. The mobility augmentation system 130 includes software modules such as an intent label determination module 230, a preprocessing module 240, a calibration module 250, an actuation determination module 260, a responsive optimization module 261, and an activity prediction module 270, and a machine learning model training engine 271. The activity prediction module 270 further includes machine learning models such as a general movement model 272, a task-specific model 273, and a user-specific model 274. The mobility augmentation system 130 may have alternative configurations than shown in FIG. 2, including different, fewer, or additional components. For example, one or more of the databases 200, 210, or 220 may be stored remotely rather than on the mobility augmentation device (e.g., contents stored in the training database 140) and may be accessible through the network 160. In another example, an additional report generation module may generate a report of the applied actuation and the monitored movement data associated with the actuation and provide the report to the remote therapy system 150.

The intent label database 200 stores labeled motor intent data. The machine learning model training engine 271 may use the data stored in the intent label database 200 to train one or more of the machine learning models used by the activity prediction module 270. The data stored in the intent label database 200 may be user-specified, determined by the mobility augmentation system 130, or a combination thereof. In some embodiments, a human administrator of the mobility management system 110 manually labels motor intent data and provides the labeled data for storage in the intent label database 200 via the network 160. Additionally or alternatively, the data stored in the intent label database 200 is motor intent data measured by the sensors 123 and labeled by the intent label determination module 230.

Label types may be associated with specific muscles or motions of muscles. The motor intent data within the intent label database 200 may be labeled according to varying degrees of specificity. Examples of general movement labels include "jump," "stand," "walk," and "step backward." Activity-specific movement labels can include "putt," "forehand swing," and "arabesque." Muscle-specific movement labels can include "knee joint extension" and "hip flexion." One or more labels may be applied to motor intent data. For example, a set of motor intent data may be labeled with "walk," "knee joint extension," and "hip flexion."

The template database 210 stores templates for the mobility augmentation devices 120a and 120b to implement templated sequencing. Template types may be associated with specific phenotypic traits or activities. For example, the template database 210 may store a template for an activity such as jumping. In another example, the template database 210 may store a template for users of a particular weight or age range. A template may include target movement signals such as target kinematic, foot pressure, or kinetic signals. In some embodiments, the templates are pre-determined. For example, the templates can be provided by the mobility management system 110 over the network 160.

In some embodiments, the mobility management system 110 determines the templates and provides the determined templates to the mobility augmentation devices 120a and 120b. The mobility management system 110 may access a particular set of movement data to generate a corresponding template. For example, the mobility system 110 may receive movement data from the augmentation device 120a and 120b to create templates that are user-specific. Additionally, the mobility management system 110 may identify particular phenotypic traits across users and generate phenotype-specific templates based on those users' movement data. For example, the mobility management system 110 identifies users who are within the ages 60-65 years old and analyzes their movement data to identify templates for general movements such as walking, standing, sitting, or grasping. To generate activity-specific templates, the mobility management system 110 accesses movement data collected across a neurotypical population performing a particular activity, such as a jump.

The mobility management system 110 then analyzes the accessed movement data for the start and end of specific muscle firing events such as the start and end of the right shank crossing a given degree of flexion. The mobility management system 110 associates or maps a start or end of the muscle firing events to respective triggers or actuation signals. For example, the end of the right shank crossing 30 degrees of flexion in a negative direction may be associated with an actuation signal applied to an actuator located at the right gastrocnemius. The mobility management system 110 may then aggregate these mappings into a template, which the system 110 provides to the mobility augmentation devices 120a and 120b.

The personalized actuation database 220 stores user-specific modifications to generalized actuation strategies. The responsive optimization module 261 may determine adjustments to generalized actuation strategies provided by the mobility management system 110. The responsive optimization module 261 may store successful adjustments (i.e., updated actuation signals that minimized the difference between target and measured movement) in the personalized actuation database 220. The user-specific modifications may include adjustments to actuation strategies with predefined actuation parameters such as an FES signal amplitude, a timing of signal application, actuators used (i.e., in an arrayed actuation configuration where an array of actuators is used to augment movement), an actuation type, any suitable characteristic defining the actuation strategy, or a combination thereof. Additionally, the personalized actuation database 220 may store user-specific calibration settings determined by the calibration module 250.

The intent label determination module 230 uses computer vision to derive labels from measured motor intent data. The intent label determination module 230 may learn the appropriate label or labels for measured motor intent data via reinforcement learning. The intent label determination module 230 may be rewarded for its label determination after measured movement data associated with the applied actuation and the determined label results in minimal differences between the measured movement and the target movement. The intent label determination module 230 provides correctly labeled motor intent data to the intent label database 200. If the label is incorrect, the motor intent data will not be stored into the intent label database 200 with the incorrect label.

The intent label determination module 230 may use a combination of one or more of computer vision, foot pressure measurements, IMU data, EMG data, and pre-defined labels to determine a label. For example, the intent label determination module 230 may determine a label for motor intent data based on a weighted combination of a label determined from reinforcement learning and manually labeled motor intent data, where a greater weight is placed upon similarities between monitored motor intent data and the manually labeled motor intent data. In some embodiments, the intent label determination module 230 includes a machine learning model using an unsupervised learning algorithm to identify reoccurring patterns of motor intent data within different sets (e.g., taken at different times or from different users) and recognize a potential label for the data.

The preprocessing module 240 may process the monitored motor intent data or movement data for use by other modules of the mobility augmentation system 130. The module 240 may align data received from multiple sensors in the temporal domain. For example, the module 240 aligns EMG and IMU signals measured by the sensors 123 on both mobility augmentation devices 120a and 120b such that the system 130 can determine, for a given time, the value of the EMG and IMU signals measured by both devices at that time. This alignment may be referred to herein as "time alignment." The module 240 may align measured data by determining an alignment that meets or exceeds threshold correlation value with aligned data provided by the mobility management system 110. The devices 120a and 120b may associate measured data with timestamps, which may be used to align the measured data when aggregated for use by the system 130.

The preprocessing module 240 may apply various digital signal processing (DSP) techniques to the measured data. The DSP techniques include filtering, averaging, peak-finding, down-sampling, Fourier transforms, root mean square (RMS), any suitable DSP technique, or a combination thereof. In one example, the module 240 may merge (i.e., time align) multiple channels (e.g., 2 kilohertz bandwidth channels) of EMG, IMU, and force sensitive resistor (FSR) data. The module 240 can preprocess the channels of EMG data by applying a differential filter and averaging a particular window in time (e.g., 100 milliseconds) for each channel. The module 240 down-samples and normalized the filtered and averaged data for use by the activity prediction module 270 as input to a machine-learned model. Additionally, the module 240 can apply a biomechanical model (e.g., inverse kinematics) or a machine learned model (e.g., a neural network) to EMG data processed using one or more of the techniques described herein to determine kinematic data associated with the muscle's electroactivity.

The preprocessing module 240 may transform a target movement goal to target movement signals. The target movement goal may be specified by a third party (e.g., a therapist of the remote therapy system 150 or an administrator of the mobility management system 110). Alternatively or additionally, the target movement goal may be specified by the user of the mobility augmentation devices 120a and 120b. For example, the activity prediction module 270 may determine, using measured EMG signals via the sensors 123, a user intends to make a particular movement and sets this movement as the target movement goal. Target movement goals include walking with normative kinematics, symmetric kinematics among both a user's legs, symmetric EMG profiles among both the user's legs, toe-heel running, reducing the user's energy expenditure while performing an action (e.g., walking), reducing pain caused by osteoarthritis (e.g., knee joint loading), any suitable motion of a body characterizable by signals (e.g., EMG, kinetics, kinematics, foot pressure, etc.), or a combination thereof.

In some embodiments, the preprocessing module 240 transforms the target movement goal to target movement signals that share a domain with the signal received from the sensors 123, referred to herein as the sensors' domain. The transformation of a movement goal into the sensors' domain is applicable in a feedback loop such as the loop depicted in FIG. 3. For example, a target movement goal of reducing knee joint loading may be transformed to various target movement signals in the sensors' domain. The various target movement signals may include a 60-degree flexion at 70% of the gait cycle or a specific rectus femoris EMG RMS profile. The preprocessing module 240 may perform the transformation using a predetermined mapping between the goals and signal. In some embodiments, the preprocessing module 240 implements an algorithm that determines likely target movement signals to achieve the target movement for the user. For example, the preprocessing module 240 may input parameters characterizing the user (e.g., phenotypic characteristics) into an algorithm to determine likely target movement signals.

The calibration module 250 optimizes the actuators 122 and sensors 123 to personalize the movement augmentation to the user. Initial calibrations may be applied before and during the monitoring taken by the sensors 123 or the actuation applied by the actuators 122. In some embodiments, the calibration module 250 optimizes electrical activity measurements taken by the sensors 123 and FES applied by the actuators 122 by performing impedance matching at the locations on the body where the sensors 123 and the actuators 122 are located. Additionally, the calibration module 250 may apply a set of calibrating actuation signals and measure the resulting movements via the sensors 123 to determine initial adjustments to generalized actuation strategies. For example, the calibration module 250 may weaken the amplitude or intensity of actuation signals applied to a user whose build is smaller than average for the user's age group and whose movement may be overcompensated when a generalized actuation strategy is applied. Measurements and adjustments made by the calibration module 250 may be stored within the personalized actuation database 220. The stored data may be accessed by the machine learning model training engine 271 or the mobility management system 110 to train a personalized machine learning model.

The actuation determination module 260 determines, based on the intended movement predicted using the activity prediction module 270, an actuation strategy to apply via the actuators 122. To determine the actuation strategy to apply, the actuation determination module 260 may determine the type of actuation to apply and then determine a strategy of that actuation type. Additionally, the actuation determination module 260 further optimizes the determined strategy using the responsive optimization module 261.

The actuation determination module 260 may determine a type of actuation to apply before determining the actuation strategy. Actuation types may include manual triggering, amplification, contralateral replay, body-to-body coaching, and templated sequencing. The actuation determination module 260 may receive a request or instructions from the user (e.g., using an input interface on the mobility augmentation device 120a specifying the desired actuation type. For example, the module 260 may receive a user's request to apply a one-time FES signal at the actuators 123, determining that the type of actuation to apply is of the manual triggering type. In some embodiments, the module 260 determines not to apply a requested manual triggering of movement augmentation. The module 260 may determine that the requested movement augmentation interferes or is unnecessary given the user's current posture or motion. For example, the module 260 receives a request from a third-party operator to trigger actuation that would assist the user in standing. The module 260 may leverage the sensors 123 and records of movement data to determine, based on the user's previous movements and current posture, that the user is currently standing and does not need assistance from the device 120a or 120b to stand.

If the mobility augmentation device 120a or 120b is a device that the user has not used before or is being used at a location the user has not previously applied movement augmentation to, the actuation determination module 260 may determine the actuation type is amplification. The module 260 may call upon the calibration module 250 to use amplification to gauge the user's sensitivity to actuation (e.g., FES signals or exoskeleton movement) and determine initial adjustments to default actuation strategies. Additionally or alternatively, the module 260 may receive a request from the user to activate amplification until instructed to deactivate, a user-specified period of time expires, or a threshold degree of success in movement augmentation is reached (e.g., the sensors 122 measure that the user's movement signal is within ±10% of the target movement signal).

The actuation determination module 260 may determine the actuation type is contralateral replay or body-to-body coaching in response to receiving instructions specifying a device from which target movement signals will be received from. In some embodiments, if the specified device is associated with the user, the module 260 determines that the actuation type is contralateral replay. For example, a hardware identifier of the mobility augmentation device 120b is assigned to the user's account, managed by the mobility management system 110, and the module 260 receives instructions that the mobility augmentation device 120a is to receive target movement signals from the device 120b. In some embodiments, if the specified device is associated with another user (e.g., a coach), the module 260 determines that the actuation type is body-to-body coaching. For example, a hardware identifier of the device 120b is assigned to the coach's account, managed by the system 110, and the module 260 receives instructions that the device 120a is to receive target movement signals from the device 120b.

The actuation determination module 260 may set templated sequencing as a default actuation type to be used when an alternative actuation type is not applicable. For example, when a user wearing both the mobility augmentation devices 120a and 120b has not specified to the module 260 that the desired actuation type is contralateral replay, the actuation determination module 260 may determine to use templated sequencing and an actuation strategy that follows a template stored within the template database 210.

After determining an actuation type, the actuation determination module 260 determines an actuation strategy of that type to apply via the actuators 122. The actuation strategies may be predefined by the mobility management system 110. In some embodiments, the actuation strategies are stored locally at the mobility augmentation devices 120a or 120b. An actuation strategy may define a combination of one or more actuation signals, a timing of delivery of the signals, and for an arrayed orientation of multiple actuators coupled to the mobility augmentation system 130, which actuators are used to apply the signals. Each actuation strategy may be mapped to a corresponding predicted movement. For example, the activity prediction module 270 determines, based on monitored motor intent data, that the user is likely intended to grasp an object and in response, the actuation determination module 260 determines an actuation strategy that is mapped to the predicted movement of grasping. The module 260 may access the personalized actuation database 220 to use a personalized actuation strategy in place of a default actuation strategy (e.g., provided by the mobility management system 110) or access the database 220 to store modified actuation that was determined using the responsive optimization module 261.

In a first example of applying an actuation strategy, the actuation determination module 260 follows a template. A machine-learned model of the activity prediction module 270 may determine a movement prediction. The module 260 determines a template associated with the determined movement prediction, the template including mappings of muscle firing events to actuation signal triggers. For example, one of the muscle firing events in the template corresponds to when the right shank crosses 30 degrees of flexion in the negative direction. The mapped actuation signal trigger may correspond to stimulating the right gastrocnemius muscle with an FES signal at 30% of the maximum FES intensity. The module 260 may then use the motor intent data or monitored movement data to identify muscle firing events in the template performed by the user and apply respective triggers.

In second and third examples of applying an actuation strategy, the actuation determination module 260 applies an actuation strategy that is not necessarily associated with a template. In the second example, the module 260 increases the tension of an ankle-foot orthosis, which may be either one of the mobility augmentation devices 120a or 120b, by a predefined amount (e.g., specified by the mobility management system 110) in response to a machine-learned model of the activity prediction module 270 predicting an intended movement of "life from chair" with at least 30% confidence. As referred to herein, the terms "intended movement" and "movement prediction" maybe used interchangeably to refer to an output of a machine-learned model configured to determine a likely movement based on motor intent data. In the third example, the module 260 reverses contraction motors of a prosthetic hand, which may be either one of the devices 120a or 120b, in response to a machine-learned model of the module 270 predicting an intended movement of "release grip" with at least 60% confidence.

The responsive optimization module 261 of the actuation determination module 260 tailors generalized actuation strategies for the user. After the actuators 122 apply the actuation strategy determined by the module 260, the sensors 123 monitor the user's movements to determine additional actuation to achieve the target movement. In some embodiments, the module 261 receives manually input feedback in addition to or as an alternative to using the sensors 123. For example, the mobility augmentation devices 120a and 120b may have an input interface including a button for the user to indicate that the applied actuation strategy was uncomfortable or to stop the applied actuation strategy. The module 261 may use this manually input feedback to determine adjustments to existing actuation or additional actuations.

The responsive optimization module 261 may determine which additional actuations or adjustments contribute to improving the movement augmentation and store those actuations or adjustments in the personalized actuation database 220 for future application. For example, the module 261 determines, based on monitored movement data by the sensors 123, that the additional actuation associated with a particular actuation strategy minimizes the difference over time between the measured movement and target movement. The module 261 then stores a record of the actuation in the personalized actuation database 220, which may be accessed to apply when the particular actuation strategy is next applied. The responsive optimization module 261 may use statistical optimization, reinforcement learning, or a combination thereof.

In one example of applying statistical optimization, the responsive optimization module 261 may use curve fitting to optimize a particular actuation strategy. The module 261 calculates a fit of the measured movement data (e.g., kinematics) of the user to a desired model (e.g., a target movement signal obtained from contralateral movement or a template). The module 261 then uses the calculated fit to adjust parameters of the actuation strategy to achieve maximal fit. For example, the module 261 may adjust the timing at which actuation signals are applied, delaying or advancing the delivery of signals as compared to a predefined timing schedule described in an actuation strategy.

A reinforcement learning approach may be used to optimize the actuation strategies as they are applied. The responsive optimization module 261 may create a set of rewards and penalties around certain features in measured movement data. Machine-learned models of the activity prediction module 270 may identify intended movements in the measured movement data. The identified intended movements may be features that are desired or unwanted given the goals of the actuation strategies applied. For example, if a machine-learned model identifies toe dragging movement in measured movement data taken after an actuation strategy associated with taking a step is applied, the module 261 may create a penalty to the actuation strategy around the toe dragging. In another example, gait symmetry may be used by the module 261 as a metric for rewarding and optimizing the actuation strategy. A movement pattern of a right, less-impacted leg may be used as a reference for scoring the left, impacted leg. The module 261 may compare the gait taken by the movement patterns of the left and right legs and use the comparison to vary the timing of when actuation signals are applied to the left leg to obtain a match between the gaits. For example, the more symmetric the gaits appear, the less the module 261 may need to vary the firing time or the module 261 may decrease timing variations by smaller amounts with each successive variation.

The activity prediction module 270 maintains one or more machine-learned models for determining an intended movement based on monitored motor intent data. The machine-learned models may include the general movement model 272, the task-specific model 273, and the user-specific model 274. The machine learning model training engine 271 of the module 270 trains the machine learning models to determine a user's intended movement using different types of data sets, where the data set type is associated with a degree to which a model is tailored to the user. For example, the training engine 271 may use a data set that is unique to an activity of jumping, and the model trained using the data set is tailored to determine that a user intends to jump. The machine learning models are configured to receive, as input, monitored motor intent data (e.g., EMG signals) and output a likely value of an IMU signal at a time in the future (e.g., a second ahead of the current EMG signals). The machine-learned models may also output a confidence score corresponding to the intended movement.

The machine learning model training engine 271 may train a machine learning model in multiple stages. In a first stage, the training engine 271 may use generalized motor intent data collected across one or more users (e.g., a neurotypical population) to train the machine learning model. The intent label determination module 230 may label the generalized motor intent data with an intent label representative of the intended motion characterized by the generalized motor intent data. The training engine 271 then creates a first training set based on the labeled generalized motor intent data. The training engine 271 trains a machine learning model, using the first training set, to determine a movement prediction. That is, the machine learning model is configured to receive, as an input, monitored motor intent data (e.g., from the sensors 123), and output the movement prediction corresponding to the likely motion characterized by the monitored motor intent data. The likely motion may include a likely IMU data value at a time occurring after a time when the motor intent data is monitored.

In a second stage of training, the training engine 271 uses user-specific motor intent data collected by the sensors 123. The machine learning model training engine 271 creates a second training set based on previously determined movement predictions and the user-specific motor intent data. The movement predictions, depending on the success of the actuation strategies applied based on the movement predictions, may serve as labels for the user-specific motor intent data. If a previously determined movement prediction resulted in successful movement augmentation, the training engine 271 may create the second training set that includes user-specific motor intent data labeled with the determined movement prediction. The training engine 271 then re-trains the machine learning model using the second training set such that the machine learning model is customized to the user's motions.

To create a training set, the machine learning model training engine 271 may determine one or more feature vectors associated with a combination of different muscles and the timing of their firing during the intended motion. For example, the training engine 271 may determine a feature vector characterizing muscle firing events associated with a certain degree of knee flexion and a toe off event during a gait cycle. In some embodiments, the training engine 271 may receive calibration data associated with calibration performed prior to actuation and the resulting movement affected by the actuation. The training engine 271 may use the calibration data in creating the training set such that the trained machine-learned model is further customized to the user's motions.

In some embodiments, the machine learning model resulting from the second stage of training is maintained as a separate machine learning model from the model resulting from the first stage of training. For example, the general movement model 272 is the model resulting from the first stage of training and the user-specific model 274 is the model resulting from the second stage of training. Additionally, the task-specific model 273 may be the model resulting from the second stage of training when the motor intent data used in the second stage is specific to a task performed by the user.

Machine learning models of the activity prediction module 270 may use various machine learning techniques such as linear support vector machine (linear SVM), boosting for other algorithms (e.g., AdaBoost), neural networks, logistic regression, naïve Bayes, memory-based learning, random forests, bagged trees, decision trees, boosted trees, boosted stumps, a supervised or unsupervised learning algorithm, or any suitable combination thereof. The machine learning models may have access to a broader set of features on which to train. The models may use physiological simulation as a component for determining a movement prediction associated with an optimal actuation strategy.

The general movement model 272 is trained by the machine learning model training engine 271 using motor intent data collected across a neurotypical population performing a variety of general movements. The general movements may include walking, standing (i.e., from a sitting position), sitting, ascending or descending steps, grasping, any suitable movement used in day-to-day activity, or a combination thereof.

The task-specific model 273 is trained by the machine learning model training engine 271 using motor intent data collected across a neurotypical population performing a specific task or gesture. The specific task may be a single type of movement that the general movement model 272 is trained to identify (e.g., walking or a gait cycle associated with walking). In some embodiments, the specific task is unique to an activity such as the performing arts or sports. For example, the task-specific model 273 may be trained to identify when a dancer intends to perform an arabesque.

The user-specific model 274 is trained by the machine learning model training engine 271 using motor intent data collected from the sensors 123. The model 274 may be obtained by re-training the general movement model 272 using monitored motor intent data collected from the user of the augmentation device 120a. Because the model 274 is trained on user-specific motor intent data, the model 274 enables the mobility augmentation system 130 to be personalized to the user and improve its accuracy in identifying movements that the user intends.

Although the activity prediction module 270 is depicted as being a component of the mobility augmentation device 120a, the mobility management system 110 may have a similar functionality. The mobility management system 110 may create training sets based on monitored motor intent data associated with different users or different tasks. The system 110 may train a model similar to the task-specific model 273 or user-specific model 274 and provide the trained models to the mobility augmentation devices 120a and 120b. The system 110 may apply a machine-learned model to determine a movement prediction based on monitored motor intent data provided by the device 120a or 120b and provide the prediction to the mobility system 130 via the network 160. In one example, motor intent data measured by the sensors 123 are stored in a local SD memory card at the device 120a, the mobility system 130 uploads data from the SD card to a cloud server (e.g., the training database 140), and the system 110 accesses the training database 140 to re-train and finetune a machine-learned model. The system 110 may be hosted on a remote computing device such as a smartphone.

Figure 3:
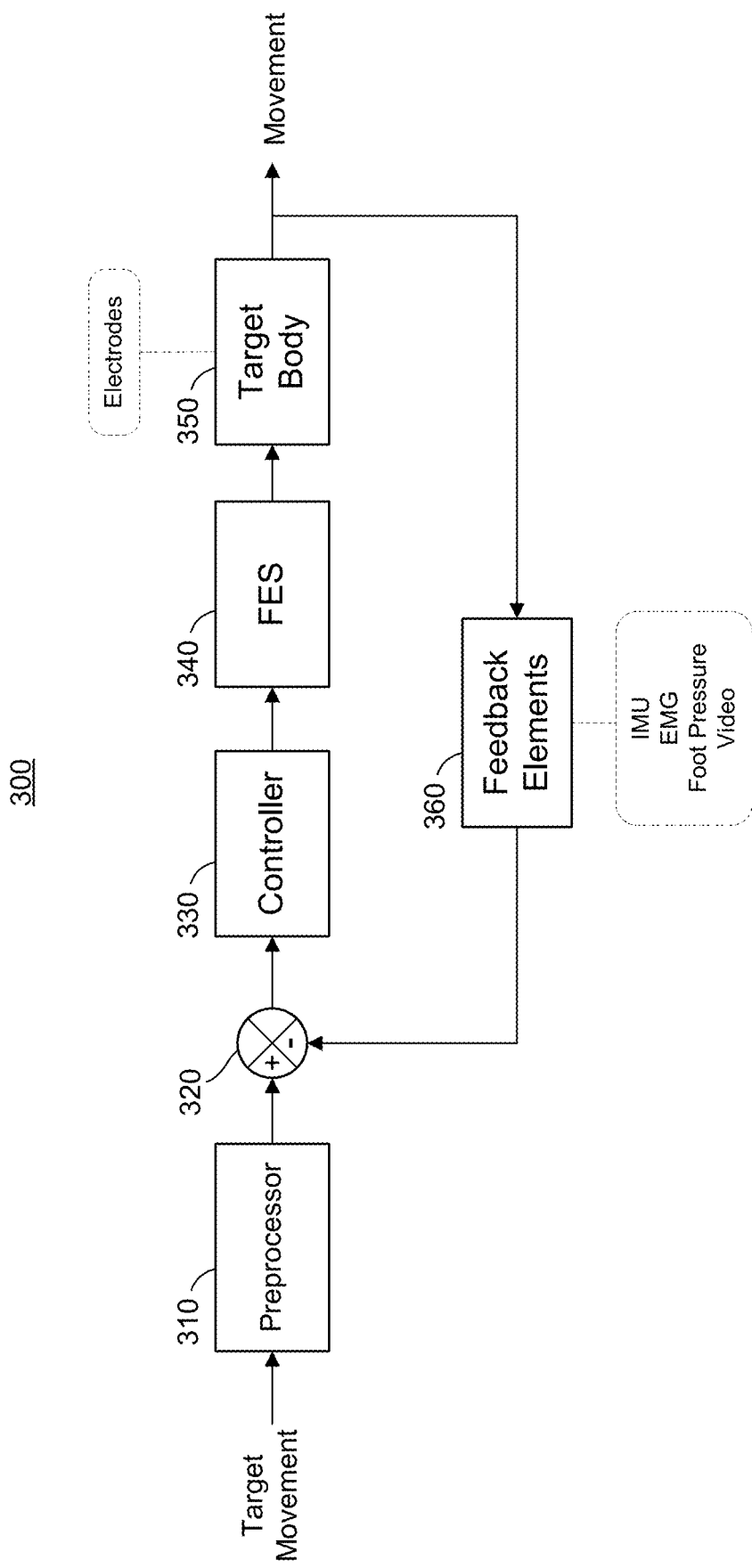
FIG. 3 is a block diagram of a feedback loop for optimizing actuation, in accordance with at least one embodiment.

FIG. 3 is a block diagram of a feedback loop 300 for optimizing actuation. The feedback loop 300 is a closed-loop system that minimizes differences between a user's movement and target movement. The mobility augmentation system 130 may perform the feedback loop 300. The feedback loop 300 includes a preprocessor 310, a summing point 320, a controller 330, an FES generator 340, a target body 350, and feedback elements 360. The feedback loop 300 may have alternative configurations than shown in FIG. 3, including for example different, fewer, or additional components. For example, the feedback loop 300 may include a decision point between the feedback elements 360 and the summing point 320 that determines whether to proceed to the summing point 320 or return to the preprocessing 310. In this example, the mobility augmentation system 130 may determine, using the output of the feedback elements 360 (i.e., the feedback signal) that the user has changed his movement goal. The changed movement goal may be input into the preprocessor 310 to determine an alternative set of target movement signals.

The system 130 receives a target movement goal as an input to the feedback loop 300. For example, the target movement goal may be received by the mobility augmentation device 120a from the user's therapist at the remote therapy system 150. The system 130 uses the preprocessor 310 to convert the target movement goal into a signal domain (i.e., the sensors' domain) for summation by the summing point 320. The preprocessor 310 may have similar functionality with the preprocessing module 240. For example, the preprocessor 310 may perform various DSP techniques such as filtering and down-sampling on the received target movement signals. The preprocessor 310 may transform a target movement goal into one or more target movement signals corresponding to the target movement goal (e.g., kinematic signals representing the movement in the movement goal).

The summing point 320 subtracts a feedback signal measured by the feedback elements 360 from the preprocessed target movement signal. The mobility augmentation system 130 then inputs the resulting error signal into the controller 330. The controller 330 may have similar functionality with the controller 121. In some embodiments, the controller 330 is a proportional-integral-derivative (PID) controller that adjusts coefficients in the control function to minimize the value of the error signal it receives over time. Additionally or alternatively, the controller 330 applies any one of the responsive optimization techniques of the responsive optimization module 261. The mobility augmentation system 130 may apply Machine Learning Control to design or tune the controller 330. For example, the controller 330 may be a Fuzzy Logic controller that is optimized, using machine learning, based on data from multiple users or to personalize the controller for a single user.

The mobility augmentation system 130 provides the output of the controller 330 to the FES generator 340. The system 130 uses the FES generator 340 to generate actuation signals to apply to the target body 350. The FES generator 340 may determine, based on the output of the controller 330, parameters for the actuation signals such as the amplitude, frequency, pulse width, or pulse shape of the actuation signal (i.e., the FES). The system 130 may apply the FES using actuator electrodes located at particular positions on the target body (e.g., at the gastrocnemius muscle of the right leg).

The mobility augmentation system 130 measures the movement resulting from or augmented by the FES using the feedback elements 360. The feedback elements may include the sensors 123, which may include an IMU sensor, an EMG sensor, a foot pressure bed, or a camera. The feedback signal is input to the summing point 320 to be subtracted from a subsequent value of the target movement signal to obtain an updated error signal.

Mobility Visualization and Reporting

Figure 4:
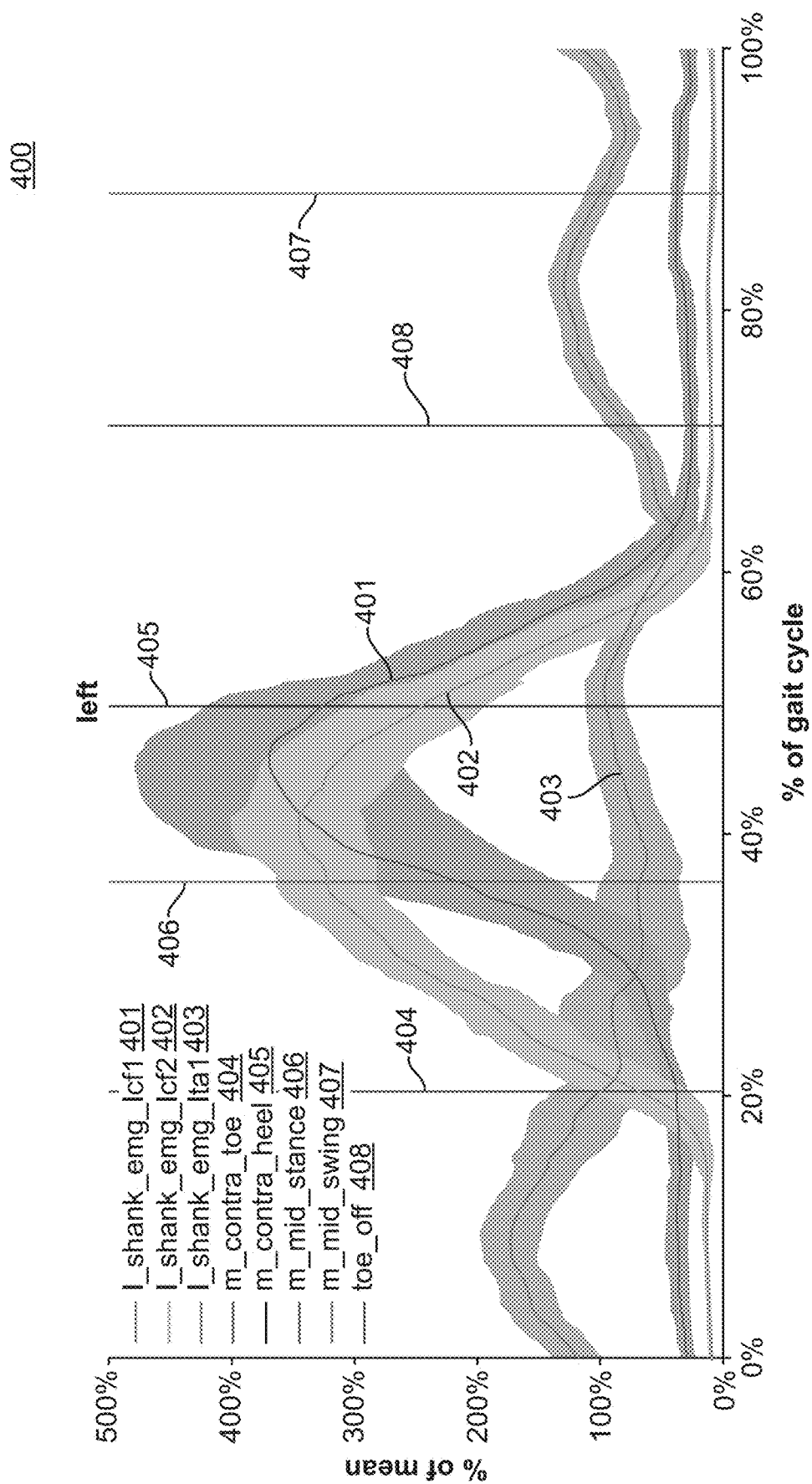
FIG. 4 depicts a visualization of electrical activity of muscles involved in a user's gait, in accordance with at least one embodiment.
Figure 5:
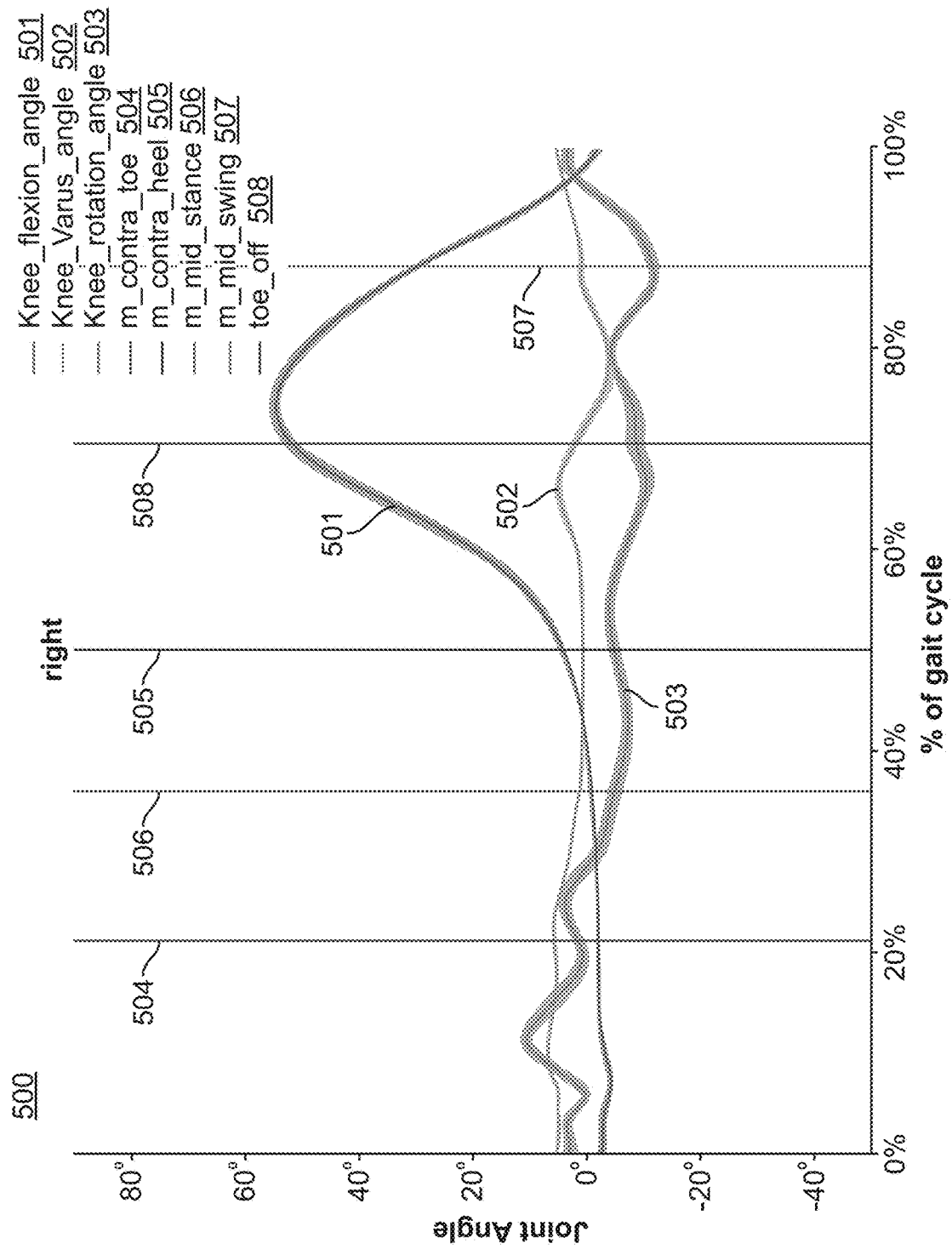
FIG. 5 depicts a visualization of kinematics of muscles involved in a user's gait, in accordance with at least one embodiment.
Figure 6:
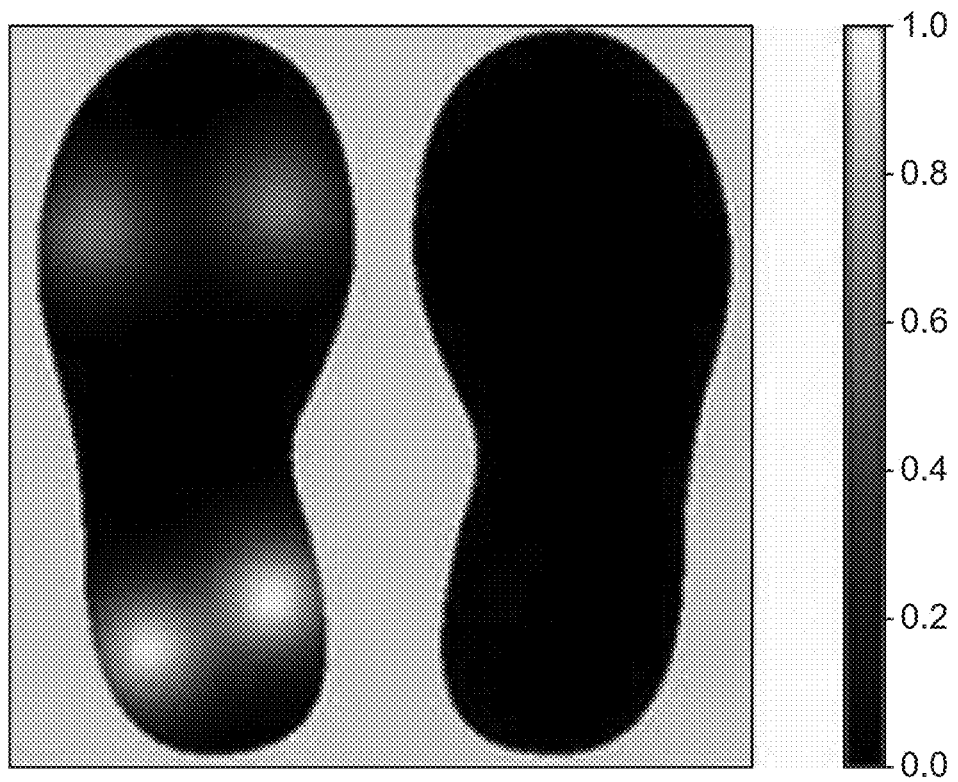
FIG. 6 depicts a visualization of foot pressure reported by the mobility augmentation system during a user's gait, in accordance with at least one embodiment.

FIGS. 4-6 depict visualizations 400, 600, and 700, respectively, of data measured by sensors of a mobility augmentation device. The visualizations 400, 600, and 700 may be included in a report generated by the mobility augmentation system 130 and provided to the mobility management system 110 or the remote therapy system 150. For example, a physical therapist using the remote therapy system 150 may request a report summarizing the user's gait cycle to assess the user's recovery from a leg injury. The report may include the visualization 400 indicating the electroactivity in muscles involved in a gait cycle, the visualization 600 indicating the kinematic signals in muscles involved in the gait cycle, and the visualization 700 indicating foot pressure during the gait cycle.

The visualization 400 depicts a gait cycle represented with EMG data. The EMG data represents the activation of a user's lower leg muscles. The visualization 400 includes signals 401-403 that represents the gait cycle over time and time points 404-408 that represent specific points of clinical significance during the gait cycle, including toe off, heel strike, mid stance, and mid swing. The visualization 400 shows, for each of the signals 401-403, the EMG signal amplitude of the gastrocnemius, one of the calf muscles, as a percentage of the average EMG signal amplitude over a gait cycle. The x-axis shows percent of gait cycle where 0% is a heel strike and 100% is the moment just before the next heel strike.

The EMG signal across multiple steps may be averaged together to produce the signals 401-403 representing the mean EMG profile across those steps. For example, an RMS is applied to the EMG data of each muscle and then normalized by the mean EMG RMS value during walking. The shaded area represents one standard deviation of the EMG profile across all of the steps. The signal 401 represents an averaged EMG signal measured at the left calf's gastrocnemius muscle. The signal 402 represents an averaged EMG signal measured at a more medial location of the left calf's gastrocnemius muscle. The signal 403 represents an averaged EMG signal associated with the left tibialis anterior and measured at a muscle on the front of the lower leg.

In some embodiments, the visualization 400 may be used as a template for determining actuation based on muscle firing events identified in the visualization 400. A machine-learned model of the activity prediction module 270 may identify the user's intended movement is a gait based on a set of presently-measured EMG signals measured from the same positions on the user's body at which the EMG signals 401-403 were measured. The actuation determination module 260 may compare the presently-measured EMG signals to the EMG signals 401-403 of the template to identify muscle firing events that are mapped to respective actuation strategies. In response to identifying a muscle firing event, the module 260 may apply the corresponding actuation strategy. For example, upon identifying, based on the presently-measured EMG signals, a muscle firing event corresponding to the kinematic signal 404 associated with a toe off of the user's contralateral foot, the module 260 may apply an actuation strategy associated with ankle flexion of a contralateral foot.

In some embodiments, the visualization 400 is the product of measured data (e.g., motor intent data and movement data) and application of a machine-learned model of the activity prediction module 270. For example, the general movement model 272 of the module 270 identifies that the motor intent data associated with the EMG signals 401-403 are indicative of a gait with 20% confidence while the gait is about 10% through its full cycle. As the user continues through his gait, the model 272 determines that the EMG signals 401-403 are indicative of a gait with increased confidence and identifies events within the gait cycle.

In some embodiments, as the general movement model 272 identifies events within the gait cycle, the confidence score associated with the EMG signals 401-403 indicating a gait increases. For example, the model 272 identifies the kinematic signal 404 associated with a toe off of the user's contralateral foot based on the EMG signals 401-403 through approximately 20% of the gait cycle. The model 272 may then identify the kinematic signal 406 associated with a user's leg in mid-stance based on the EMG signals 401-403 through approximately 35% of the gait cycle, the kinematic signal 405 associated with a heel strike of the contralateral foot based on the EMG signals 401-403 through approximately 50% of the gait cycle, the kinematic signal 408 associated with a toe off of the user's foot based on the EMG signals 401-403 through approximately 73% of the gait cycle, and the kinematic signal 407 associated with the user's leg in mid-swing based on the EMG signals 401-403 through approximately 89% of the gait cycle. In this way, the model 272 may determine the intended movement is a gait cycle with increasing confidence scores as the kinematic signals 404, 406, 405, 408, and 407 of the visualization 400 are identified over time.

FIG. 5 depicts a visualization 500 of kinematics of muscles involved in a user's gait. The kinematics represent the knee joint angle during a gait cycle. The kinematic signals 501-503 represent kinematics associated with flexion, varus or valgus, and rotation. The x-axis shows a percentage of gait cycle where 0% is heel strike and 100% is a moment just before the next heel strike. The kinematics (i.e., the knee joint angle) are measured across multiple steps to produce the data shown in the visualization 500 of an average gait cycle. The signal 501 represents the average knee flexion angle, the signal 502 represents the average knee varus or valgus, and the signal 503 represents the average knee rotation during the average gait cycle. The time points 504-508 are represented as vertical lines that demarcate typical points of clinical significant during the gait cycle including toe off, mid stance, and mid swing as well as toe off of the contralateral leg and heel strike of the contralateral leg.

FIG. 6 depicts the visualization 600 of foot pressure reported by the mobility augmentation system 130 during a user's gait. The sensors 123 may include a foot pressure bed. The mobility system 130 may use movement data measured at the foot pressure bed to obtain the visualization 600. The visualization 600 shows foot pressure normalized by the maximum pressure value during the measurement. Alternatively, the mobility augmentation system 130 may normalize the foot pressure data using the mean foot pressure values during an activity, the maximum foot pressure during an activity (e.g., during quiet standing), or any suitable measurement of foot pressure. Although depicted as normalized, the visualization 600 may also be represented by un-normalized units of pressure (e.g., Pascals). At the instance of time shown in the visualization 600, the user is striking his heel to the ground, causing a greater pressure at the heel than at the sole. Just as the actuation determination module 260 can use the data of the visualization 400 to identify a muscle firing event within a movement and determine a corresponding actuation strategy, the module 260 may also use the data of the visualization 600 to determine an appropriate actuation strategy. For example, the maximum pressure at the heels may be indicative of a heel strike within a gait and the module 260 may apply an actuation strategy for a heel strike.

In some embodiments, the visualization 600 is the product of measured data (e.g., movement data) and application of a machine-learned model of the activity prediction module 270. For example, the general movement model 272 of the module 270 identifies that the movement data measured using a foot pressure bed is indicative of a heel strike of a gait cycle with 70% confidence. The machine learning model training engine 271 may use visualizations such as the visualization 600 to train the model 272 to identify events at the feet such as a toe off or heel strike.

In some embodiments, as the general movement model 272 identifies events within the gait cycle, the confidence score associated with the movement data increases, where the movement data indicates a gait and is measured using the foot pressure bed. Although not shown, additional visualizations from data measured using the foot pressure bed over time may be used to identify various kinematic signals associated with a gait throughout a gait cycle. Similar to the intended movement identification process as described in the description of the visualization 400, the model 272 may determine the intended movement is a gait cycle with increasing confidence scores as the foot pressure bed data over time, including the visualization 600, are analyzed over time.

Examples of Mobility Augmentation Devices

FIGS. 7-9 illustrate various wearable form factors of mobility augmentation devices such as the mobility augmentation device 120a or 120b of FIG. 1. Form factors are structured to enable personalized delivery of movement augmentation, optimize the comfort of wearing the mobility augmentation devices, and increase the efficacy of the movement augmentation.

For example, the form factors can simultaneously enable personalized delivery and increase the efficacy of movement augmentation through an array-based approach. That is, the form factor allows for multiple mobility augmentation devices to be placed around various locations of the body. After the devices are initially positioned, the mobility augmentation system may apply calibration (e.g., an actuation type of amplification) to determine the user's sensitivity to the actuation signals (e.g., FES signals) at the initial positions. The mobility augmentation system may determine that a device is positioned at a location that is not conducive to applying augmentation. For example, the user may position a device's actuating electrode closer to a bone (e.g., the ankle bone) than to a muscle (e.g., the soleus muscle of the ankle), diminishing the effects of FES actuation intended for muscle rather than bone. The mobility augmentation system may provide an indication to a user that the device placement should be adjusted.

In some embodiments, the mobility augmentation system may determine directions to provide to the user for adjusting the positioning of a mobility augmentation device. The mobility augmentation system may determine the locations of a user's mobility augmentation devices relative to one another as they are initially placed on the user's body. For example, the mobility augmentation system may use wireless communications circuitry on each device to transmit or receive radio frequency (RF) signals and determine, based on the time between transmission and receipt of an RF signal, the distance between two devices. The mobility augmentation system may determine a device is improperly positioned if, after determining a first device is properly positioned during calibration, a second device is not within a threshold range of distances from the first device, the second device's calibration results indicate poor actuation delivery, or a combination thereof. The threshold range may depend upon the target location on the body at which the device is intended to measure movement and motor intent data. For example, the user may specify, prior to positioning a mobility augmentation device, that the first device is intended to be placed at the knee and the second device is intended to be placed near the ankle.

Figure 7A:
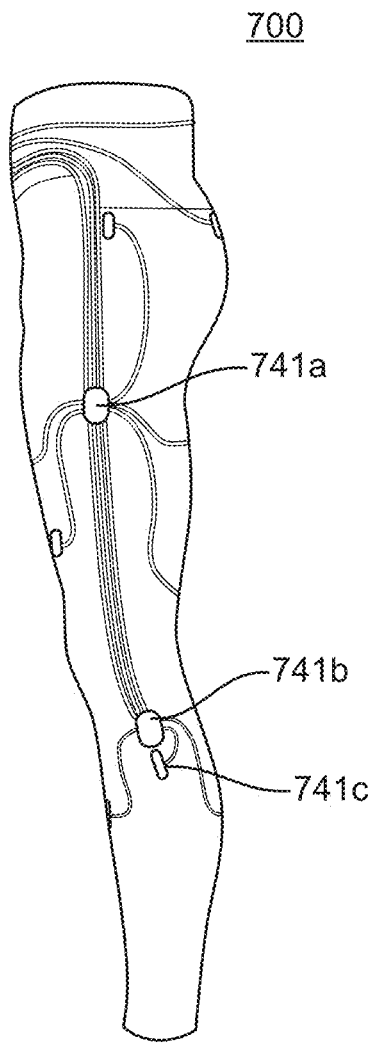
FIGS. 7A and 7B illustrate a wearable form factor of a mobility augmentation device for a user's legs, in accordance with at least one embodiment.
Figure 7B:
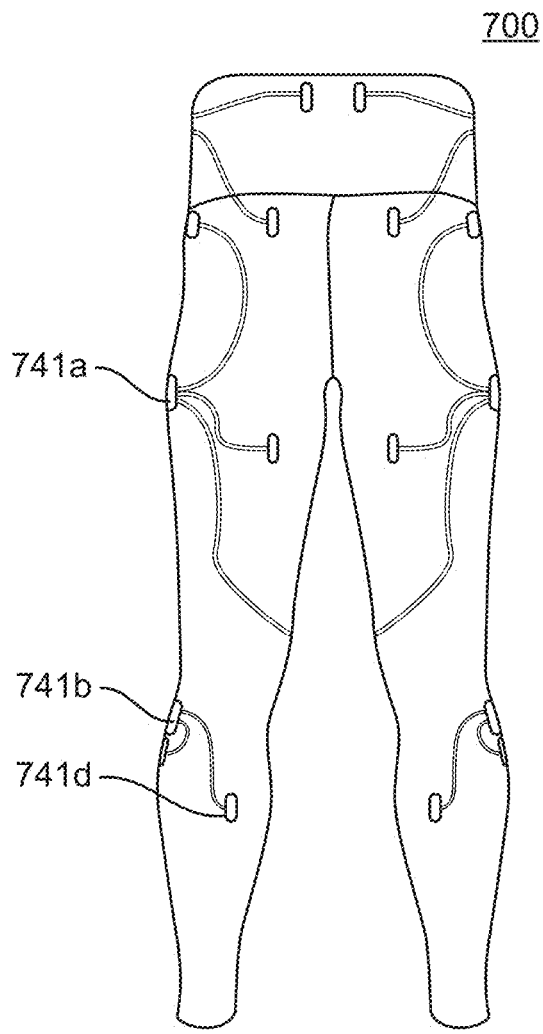

FIGS. 7A and 7B illustrate a wearable form factor 700 of a mobility augmentation device for a user's legs. The form factor 700 may be a pair of leggings that are outfitted with multiple sensors and actuators. For example, electrodes 741a-d may be either sensing electrodes to measure the electroactivity at the respective locations on the user's body or actuating electrodes to apply the actuation strategy at the respective locations.

Figure 8A:
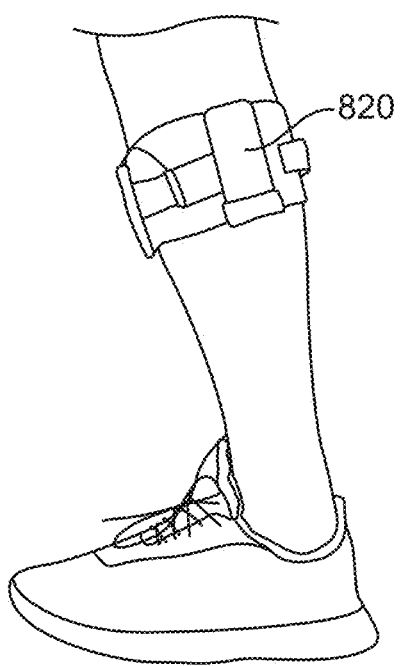
FIGS. 8A and 8B illustrate wearable, modular form factors of a mobility augmentation device, in accordance with at least one embodiment.
Figure 8B:
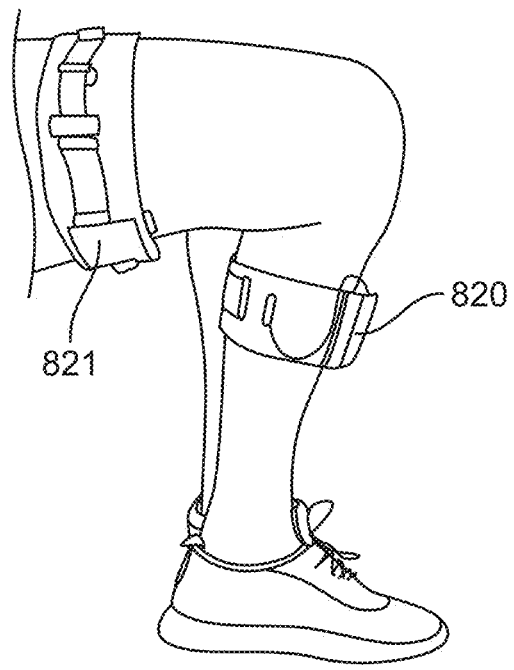

FIGS. 8A and 8B illustrate wearable, modular form factors 820 and 821 of respective mobility augmentation devices. The devices may have the same, initial form factor and be adjusted to be placed around different locations of the user's body. For example, the device with the form factor 820 is adjusted to be placed around a calf while the device with the form factor 821 is adjusted to be placed around a thigh. The modularity of the mobility augmentation devices allows the user to adjust the position of each mobility augmentation device to optimize the comfort of wearing the mobility augmentation devices. For example, a device may have a belt, Velcro strap, stretch material, any other suitable adjustable mechanism for increasing tightness around a limb to maintain position, or a combination thereof. In this way, the modular mobility augmentation devices are adjustable to be positioned comfortably at a location or fit of the user's choosing.

Figure 9A:
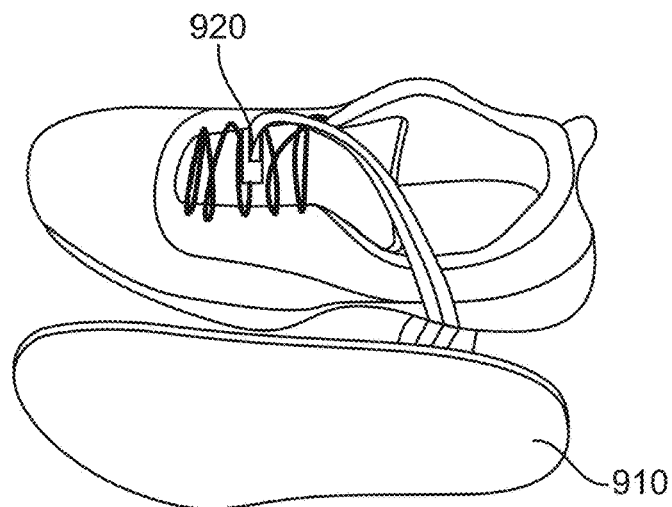
FIGS. 9A and 9B illustrate a wearable form factor of a mobility augmentation device for a user's foot, in accordance with at least one embodiment.
Figure 9B:
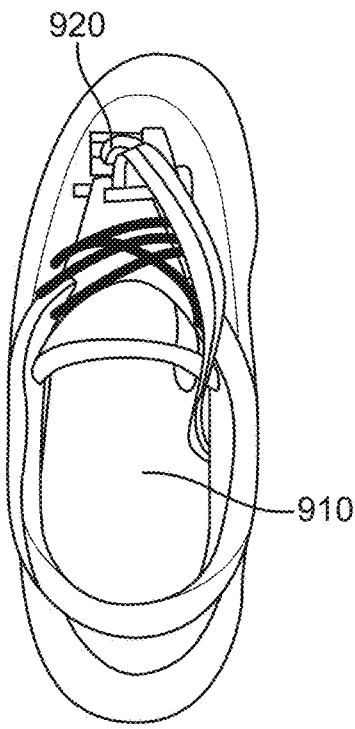

FIGS. 9A and 9B illustrate a wearable form factor 900 of a mobility augmentation device for a user's foot. The wearable form factor 900 is depicted as having a foot pressure bed sensor 910 that may be inserted and removed from the user's existing shoes or embedded into a pair of shoes that serve as the mobility augmentation device. The foot pressure bed sensor 910 may be coupled to one or more processors 920 (e.g., processors performing the functions of the mobility augmentation system 130). In one example, the mobility augmentation device 120a has the wearable form factor 700 and the mobility augmentation device 120b has the wearable form factor 900. In this way, the combination of the devices 120a and 120b can measure and apply stimulation for augmenting movement involving the legs, feet, or combination thereof.

Processes for Applying and Optimizing Mobility Augmentation Systems

Figure 10:
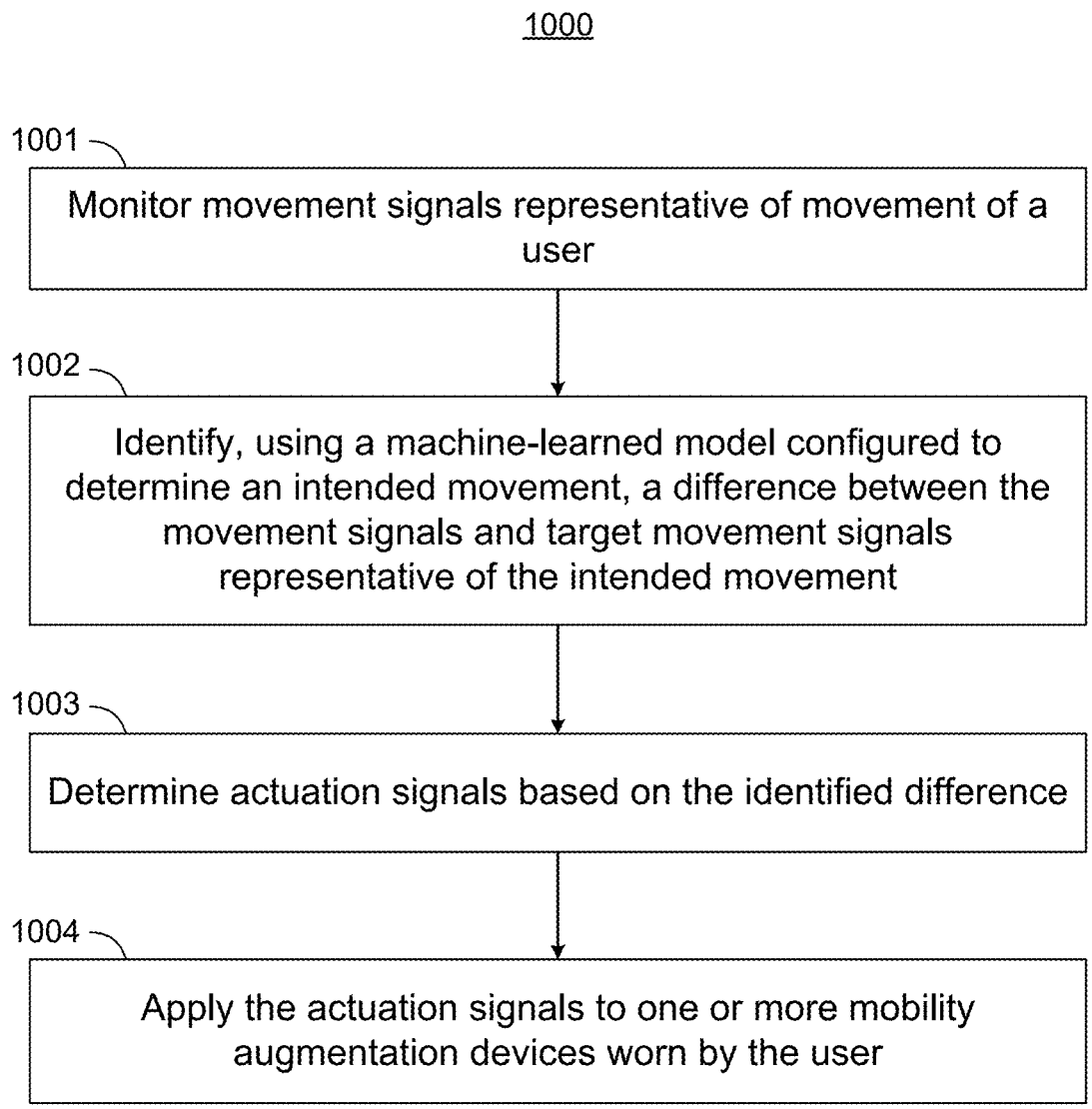
FIG. 10 is a flowchart illustrating a process for applying actuation signals to an augmentation device worn by a user, in accordance with at least one embodiment.

FIG. 10 is a flowchart illustrating a process 1000 for applying actuation signals to an augmentation device worn by a user. In some embodiments, the mobility augmentation system 130 performs operations of the process 1000 in parallel or in different orders, or performs different steps. For example, in addition to or as an alternative to determining 1003 actuation signals and applying 1004 the signals, the process 1000 may determine, based on the identified difference, a reward or penalty for an actuation strategy that contributed to the monitored 1001 movement signals. For example, if the identified 1002 difference is small, the system 130 may reward the actuation strategy used. In this way, the process 1000 maybe used to optimize how the mobility system 130 applies actuation strategies.

The mobility augmentation system 130 monitors 1001 movement signals representative of movement of a user. The system 130 is coupled to the sensors 123 that may continuously measure and provide the user's movement signals, enabling the system 130 to monitor the user's movement signals. For example, the sensors 123 include IMU sensors for measuring kinematic and kinematic data that represent the user's movement.

The mobility augmentation system 130 identifies 1002, using a machine-learned model configured to determine an intended movement, a difference between the movement signals and target movement signals representative of the intended movement. The system 130 uses a machine-learned model of the activity prediction module 270 to determine the intended movement. For example, the general movement model 272 determines, based on EMG signals measured by one or more of the sensors 123, that the user intends to make a gripping movement. Using the determined intended movement, the system 130's actuation determination module 260 determines an actuation strategy corresponding to an intention to grip an object, where the actuation strategy includes target movement signals. The target movement signals may be specified by the mobility management system 110 and be a representation of a neurotypical population performing the intended movement. The system 130 then determines a difference between the monitored 1001 movement signals and the target movement signals (e.g., the summing point 320 of the feedback loop 300).

The mobility augmentation system 130 determines 1003 actuation signals based on the identified 1002 difference. In some embodiments, the system 130 modifies parameters of previously applied actuation signals based on the identified 1002 difference to determine 1003 updated actuation signals. For example, the identified 1002 difference may be smaller than a previously identified difference and the system 130, in response to this decreasing difference, may lessen the intensity of the current amplitude of the FES actuation signals. Alternatively or additionally, the system 130 may access predefined actuation signals that are mapped to particular actuation strategies and identified differences.

The mobility augmentation system 130 applies 1004 the actuation signals to the one or more mobility augmentation devices worn by the user. In some embodiments, the system 130 uses the actuators 122 to apply the determined 1003 actuation signals to target locations on the user's body. For example, the system 130 may be communicatively coupled to mobility augmentation devices having modular form factors like the form factors 820 and 821. The system 130 on one of the devices may use a FES generator (e.g., the FES generator 340) to generate the actuation signals and apply the signals using that device's actuators. The system 130 may then transmit instructions to another device on the user's body for generating and applying the actuation signals using the other device's onboard FES generator and actuators.

Figure 11:
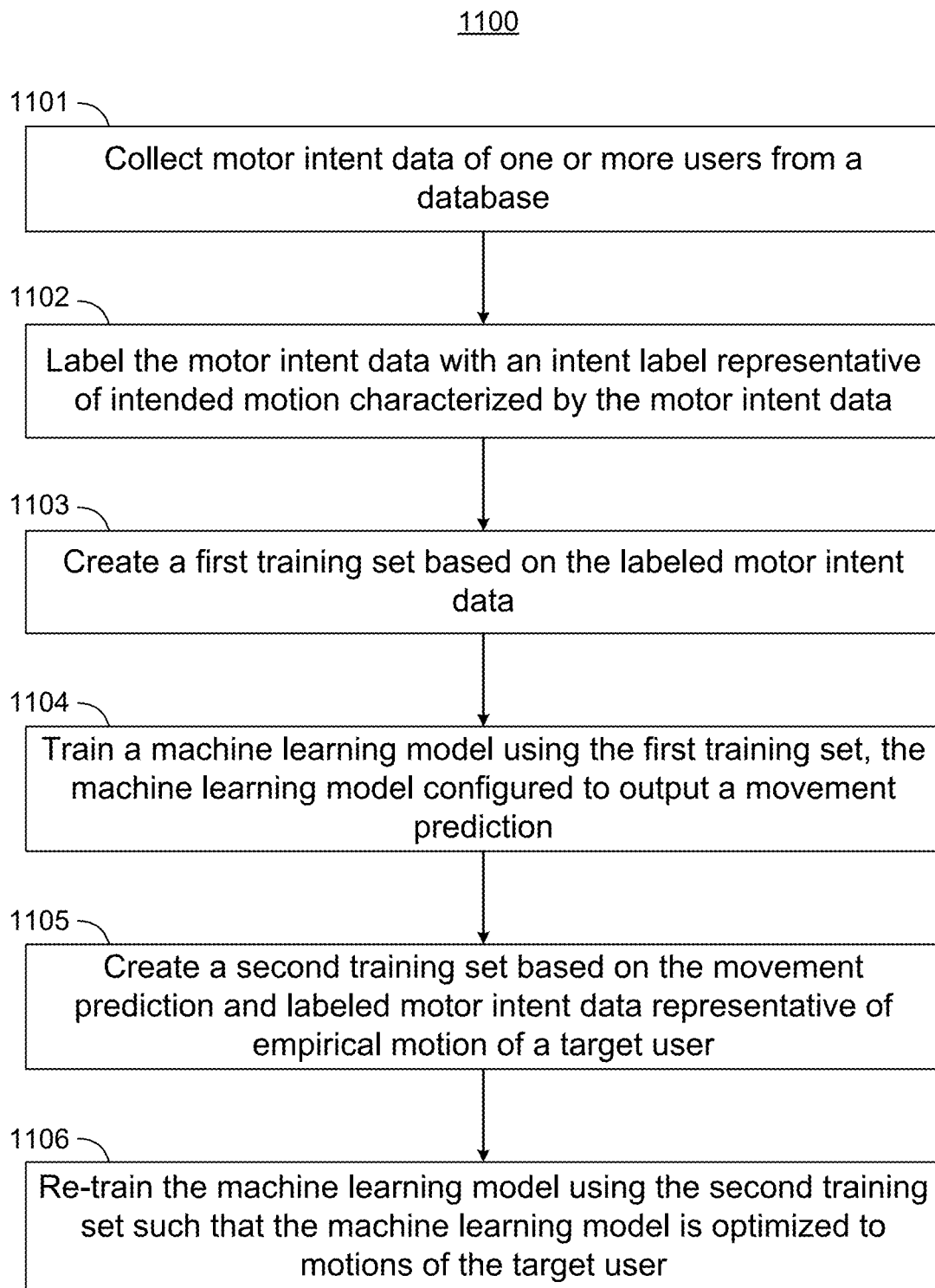
FIG. 11 is a flowchart illustrating a process for training a machine learning model configured to output a movement prediction based on monitored motor intent data, in accordance with at least one embodiment.

FIG. 11 is flowchart illustrating a process 1100 for training a machine learning model configured to output a movement prediction based on monitored motor intent data. In some embodiments, the mobility augmentation system 130 performs operations of the process 1100 in parallel or in different orders, or may perform different steps. For example, labeling 1102 the motor intent data may be preceded by determining a label for the motor intent data if the label for the collected 1101 motor intent data is not pre-specified (e.g., by the mobility management system 110).

The mobility augmentation system 130 collects 1101 motor intent data of one or more users from a database. The motor intent data may include EMG data, IMU data, foot plantar pressure signals, kinetic signals, or a combination thereof. The one or more users may have neurotypical or neuro-atypical movement. The motor intent data collected from neurotypical users may be referred to as neurotypical motor intent data while the motor intent data collected from neuro-atypical users may be referred to as neuro-atypical motor intent data. The motor intent data may represent general movements or a specific gesture (e.g., a step, grasp, lift, or contraction). The motor intent data may represent various movements performed by a target user. For example, the motor intent data can capture how the target user's left leg moves.

The mobility augmentation system 130 labels 1102 the motor intent data with an intent label representative of intended motion characterized by the motor intent data. The intent label determination module 230 of the system 130 may use computer vision to derive labels for the motor intent data. For example, the motor intent data includes videos of the one or more users performing a gesture (e.g., a step backwards) and the intent label determination module 230 uses computer vision to determine that videos share a common pattern representative of a user taking a step backwards.

The mobility augmentation system 130 creates 1103 a first training set based on the labeled motor intent data. The machine learning model training engine 271 of the mobility augmentation system 130 may generate a set of feature vectors from the motor intent data associated with the label for taking a step backwards. The feature vectors may represent various data types such as EMG, foot pressure, and IMU signals associated with the one or more users taking a step backwards. The machine learning model training engine 271 may then use the feature vectors and the label to train a machine learning model (e.g., determining a set of weights for the machine learning model).

The mobility augmentation system 130 trains 1104 a machine learning model using the first training set, where the machine learning model is configured to output a movement prediction. The machine learning model may identify general movements when trained 1104 using the collected 1101 motor intent data associated with the users' general movements. The machine learning model may determine a movement prediction for various actuation types. For example, with the contralateral replay actuation type, the movement prediction may correspond to target movement signals that are performed by the user at another location of the user's body (e.g., a contralateral leg having neurotypical movement). That is, the system 130 may receive the target movement signals from another mobility augmentation device on the user and the activity prediction module 270 may identify the movement represented by the target movement signals.

The mobility augmentation system 130 creates 1105 a second training set based on the movement prediction and labeled motor intent data representative of movement signals of a target user. The movement signals of the target user may include one or more of kinematic signals, foot plantar pressure signals, kinetic signals, or a combination thereof. The system 130 may create 1105 the second training set similarly to how the first training set was created 1103. For example, the system 130 generates a set of feature vectors from the motor intent data associated with the user's movement signals and the movement prediction of taking a step backwards to create the second training set.

The mobility augmentation system 130 re-trains 1106 the machine learning model using the second training set such that the machine learning model is optimized to motions of the target user. In some embodiments, re-training 1106 includes determining a similarity score between the user's movement signals and target motion and adjusting a strength of association between the monitored motor intent data and the movement prediction associated with the target motion. For example, the system 130 may strengthen an association between monitored motor intent data and the movement prediction in response to determining that a similarity score computed based on target movement signals and the user's movement signals exceeds a threshold. In another example, the system 130 may weaken the association between the monitored motor intent data and the movement prediction in response to determining that the similarity score failed to exceed the threshold. In some embodiments, the similarity score may indicate a degree of symmetry in the user's gait (i.e., the degree to which the left and right legs move similarly while walking).

Similarly, re-training 1106 may include adjusting a strength of association between the monitored motor intent data and the movement prediction associated with the target motion in response to identifying a wanted or unwanted movement feature in the user's movement signals. For example, the system 130 may strengthen an association between monitored motor intent data and the movement prediction in response to detecting that the user's toes turned upward during a gait, which is a neurotypical movement within a gait cycle. The system 130 may weaken an association between monitored motor intent data and the movement prediction in response to detecting that the user's toes failed to turn upward during the gait (i.e., at least one toe dragged as the user attempted the gait).

Additional Applications of Movement Augmentation

The mobility augmentation device and system described herein may improve disease management for patients of Parkinson's Disease (PD). Clinicians currently use standardized rating scales to assess a patient's condition, track disease progression, and evaluate responsiveness to treatment. The motor section of the Unified Parkinson's Disease Rating Scale (UPDRS), which is the gold standard for assessing a PD patients' motor symptoms, requires the patient to perform a series of motor tasks, which are visually evaluated by a trained personnel. Unfortunately, these rating scales are limited by poor temporal resolution and the subjective nature of scoring. Because symptom severity fluctuates throughout the day and can worsen with multitasking, clinical exams are also unlikely to capture the real-world severity of a patient's disease. The mobility augmentation device and system described herein can be used to overcome a patient's motor impairments caused by PD and optimize the patient's drug regimen for PD.

A mobility augmentation device can predict the onset of motor symptoms of PD before they occur. The device can generate an alert to the patient or augment the patient's movement to help manage PD. In some embodiments, the mobility augmentation device applies FES to help the patient overcome motor impairments such as gait freezes and tremors. The mobility augmentation device may be a four-channel FES array that activates different muscles. The location and duration of the FES can be customized to the patient's needs. The mobility augmentation device can be used to supplement gastrocnemius activation using EMG-triggered FES. With the addition of FES, the patient's gait may be restored to a neurotypical gait, overcoming impairments like gait freezes. Experimental results from applying arrayed FES stimulation is further described in the description of FIG. 14.

Pharmacological agents or chemical stimuli such as levodopa (l-DOPA) are used for the treatment of PD. The delivery of l-DOPA in a patient's drug regimen may be optimized using the mobility augmentation device and system described herein. For electronically assisted l-DOPA (eDOPA), the mobility augmentation device quantifies the patient's UPDRS score and monitors minute-to-minute tracking of motor symptoms. For example, EMG and IMU data may be continuously tracked for multiple hours, identifying tremors, freezing, and bradykinesia (i.e., slowness of movement) experienced by the patient. The mobility augmentation device can then report the monitored information to the patient's physician, enabling more timely and precise adjustments of l-DOPA.

In some embodiments, the mobility augmentation system may determine the efficacy of chemical stimulus like l-DOPA. The system may identify a physical condition of a patient and the chemical stimulus administered to the user to augment the physical condition. For example, the system uses EMG and IMU sensors to identify tremors in the patient. The system can access medical records (e.g., from a remote therapy system) to identify a drug (e.g., l-DOPA) administered to the patient that treats the identified tremors. The system may monitor motor intent data representative of the patient's intended movement, where the motor intent data is indicative of an efficacy of the chemical stimulus. For example, the system monitors EMG signals associated with the patient intended to grip an object in his hand, where the person's movement to make the grip is affected by the l-DOPA he is taking.

The mobility augmentation system may also monitor movement signals that represent the patient's movement. For example, IMU sensors outfitted in a mobility augmentation device that the patient is wearing over his hand (e.g., a glove), measure the kinematic and kinetic signals of the patient's fingers and palm as he grips the object in his hand. The system may use a machine-learned model (e.g., the task-specific model 273) to identify a difference between the monitored movement signals and target movement signals associated with gripping an object. Based on this identified difference, the system may determine the efficacy of the chemical stimulus. For example, the system may determine that the chemical stimulus is not augmenting the user's movement in response to determining that the magnitude of the identified difference exceeds a threshold magnitude. For example, the patient's tremors detected from an IMU sensor maybe associated with an identified difference that exceeds a threshold associated with minor tremors, indicating that the drug regimen needs evaluation or adjustment.

Experimental Findings

Figure 12:
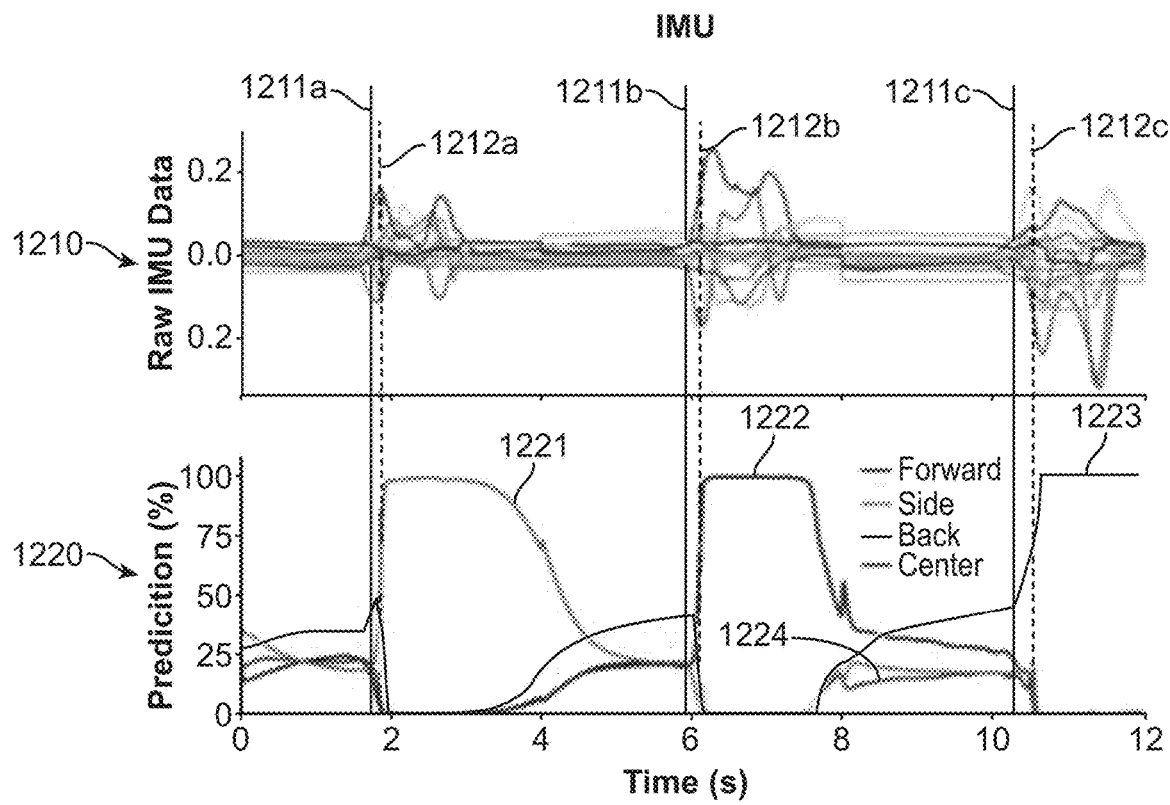
FIG. 12 shows an experimental finding of action prediction using inertial measurement unit data.

FIG. 12 shows an experimental finding of action prediction using inertial measurement unit data. A graph 1210 shows IMU data over time and a graph 1220 shows the prediction confidence over time of each of multiple potential movement predictions corresponding to the IMU data. The movement predictions in the graph 1220 include a side step prediction 1221, a forward step prediction 1222, a backward step prediction 1223, and a center step prediction 1224. The IMU data of the graph 1210 was measured by IMU sensors of the mobility augmentation device described herein. The probabilities of the graph 1220 were determined by the mobility augmentation system described herein. The system detects a user's foot lifting at a time 1211$a$ and determines the side step prediction 1221 at a time 1212$b$ with approximately 100% confidence based on the measured IMU data. The system detects a user's foot lifting at a time 1211$b$ and determines the forward step prediction 1222 at a time 1212$b$ with approximately 100% confidence based on the measured IMU data. The system detects a user's foot lifting at a time 1211$c$ and determines the backward step prediction 1223 at a time 1212$c$ with approximately 100% confidence based on the measured IMU data.

Figure 13:
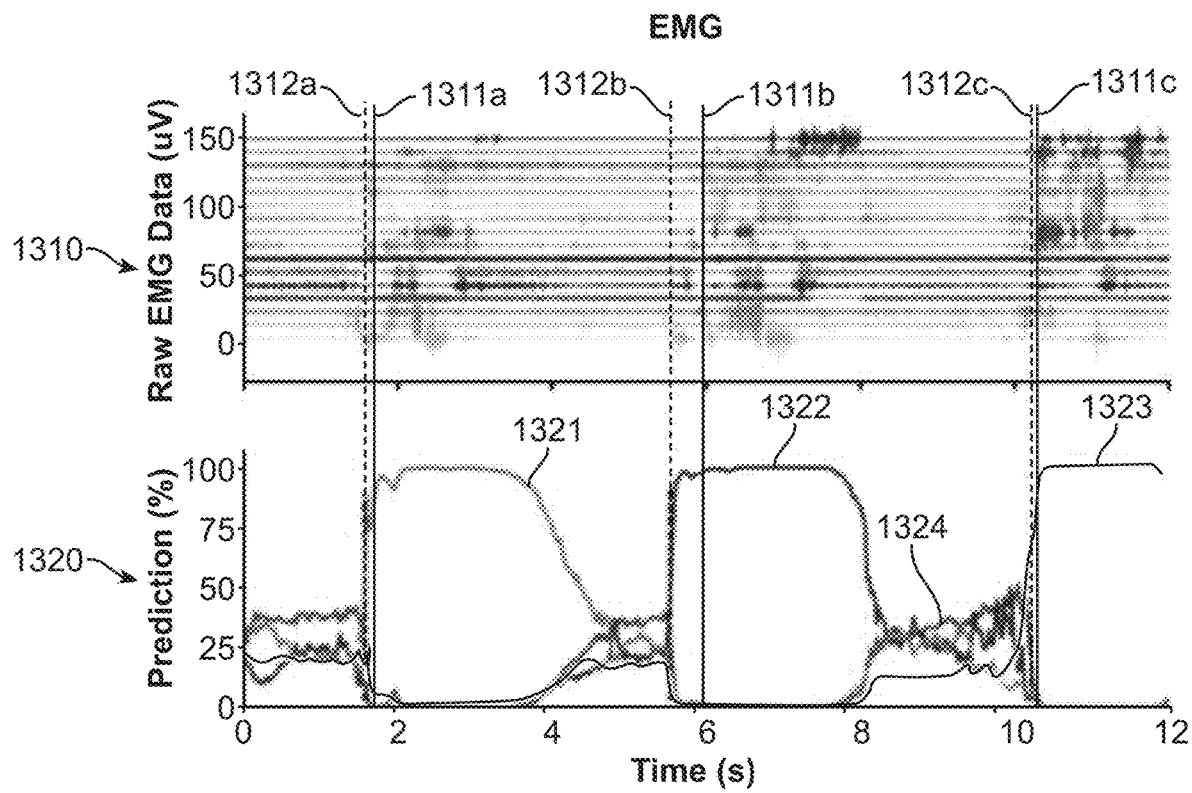
FIG. 13 shows an experimental finding of action prediction using electromyography data.

FIG. 13 shows an experimental finding of action prediction using electromyography data. A graph 1310 shows EMG data over time and a graph 1320 shows the prediction confidence over time of each of multiple potential movement predictions corresponding to the EMG data. The movement predictions in the graph 1320 include a side step prediction 1321, a forward step prediction 1322, a backward step prediction 1323, and a center step prediction 1324. The EMG data of the graph 1310 was measured by EMG sensors of the mobility augmentation device described herein. The probabilities of the graph 1320 were determined by the mobility augmentation system described herein. The system determines the side step prediction 1321 at a time 1312$a$ with approximately 100% confidence based on the measured EMG data and detects a user's foot lifting at a time 1311$a$. The system determines the forward step prediction 1322 at a time 1312$b$ with approximately 100% confidence based on the measured EMG data and detects a user's foot lifting at a time 1311$b$. The system determines the backward step prediction 1323 at a time 1312$c$ with approximately 100% confidence based on the measured EMG data and detects a user's foot lifting at a time 1311$c$.

While the times 1212$b$-$c$ that the IMU predictions shown in FIG. 12 occur after the user's actual movement, the times 1312$a$-$c$ that the EMG predictions of FIG. 13 occur are earlier than the user's actual movement. Specifically, the IMU predictions occurred approximately 103 milliseconds after the user's foot lifted off of the ground and the EMG predictions occurred approximately 269 milliseconds before the user's foot lifted off of the ground. The earlier predictions allow the actuation strategies to be applied earlier, as needed, reducing the likelihood that the actuation strategy will be ineffective because it is not timely applied according to the user's current movements being augmented. Hence, the mobility augmentation devices using EMG sensors may improve movement augmentation over solely using IMU sensors.

Figure 14:
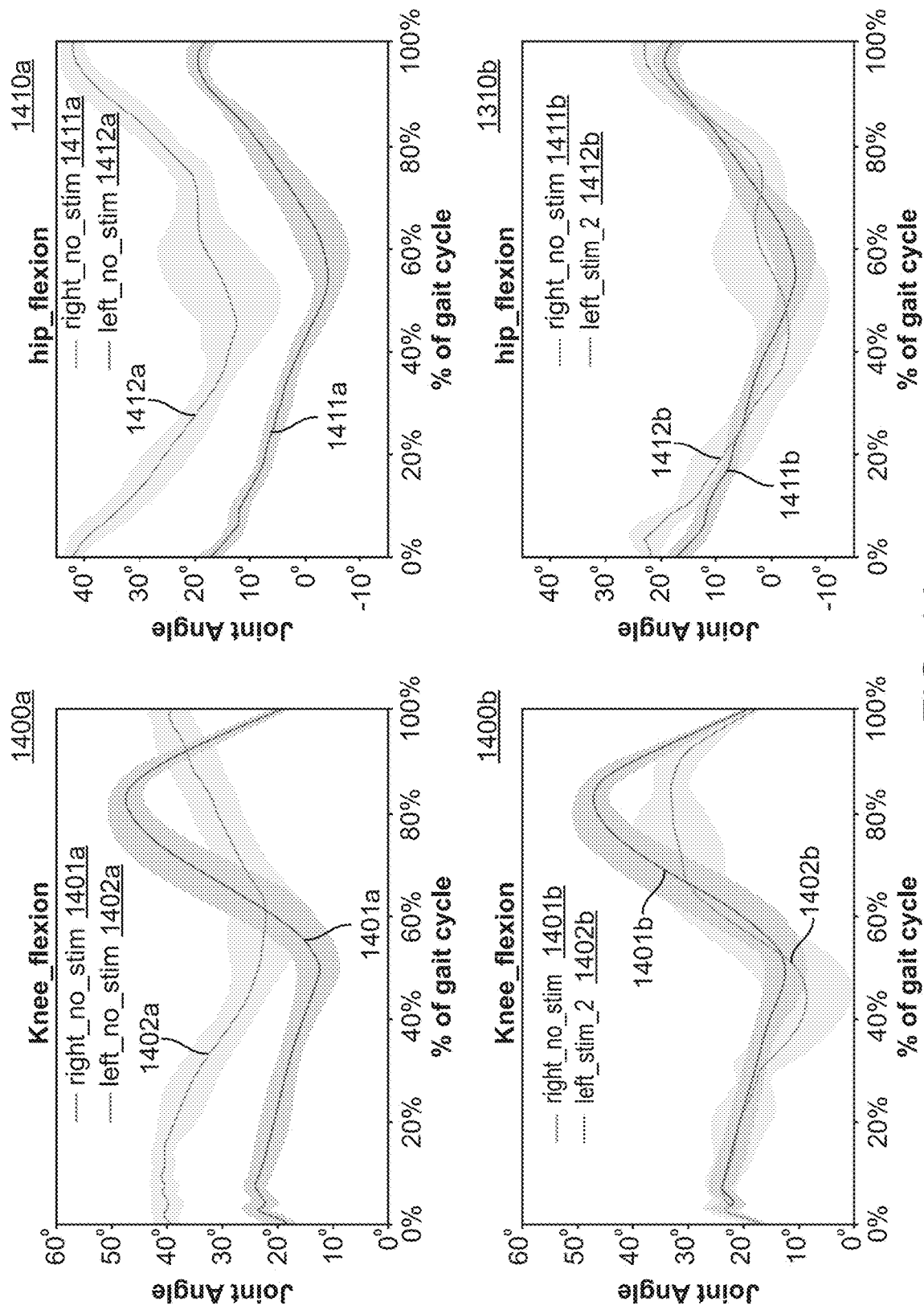
FIG. 14 shows an experimental finding of knee and hip kinematics augmented with functional electrical stimulation.

FIG. 14 shows an experimental finding of knee and hip kinematics augmented with functional electrical stimulation. A 10 year-old child with primarily unilateral spastic cerebral palsy (CP) wore the mobility augmentation devices described herein and her movements were monitored with and without FES. Her right leg showed neurotypical movement while her left leg's movement was impacted by CP. The mobility augmentation devices were positioned at each of her legs and the sensors of the devices measured kinematic signals from her gait cycle.

Graph 1400a shows her knee kinematics without FES applied. Kinematic signal 1401a of the graph 1400a shows her right knee's flexion angle exhibiting neurotypical movement. Kinematic signal 1402a of the graph 1400a shows her left knee's flexion angle exhibiting neuro-atypical movement. Graph 1400b shows her knee kinematics with FES applied. Kinematic signal 1401b of the graph 1400b shows her right knee's flexion angle exhibiting neurotypical movement. Kinematic signal 1402b of the graph 1400b shows her left knee's flexion angle augmented by FES and exhibiting movement that more closely aligns with the neurotypical kinematic signal 1401b than with the neuro-atypical kinematic signal 1402a.

Graph 1410a shows her hip kinematics without FES applied. Kinematic signal 1411a of the graph 1410a shows her right hip's flexion angle exhibiting neurotypical movement. Kinematic signal 1412a of the graph 1410a shows her left hip's flexion angle exhibiting neuro-atypical movement. Graph 1410b shows her hip kinematics with FES applied. Kinematic signal 1411b of the graph 1410b shows her right hip's flexion angle exhibiting neurotypical movement. Kinematic signal 1412b of the graph 1410b shows her left hip's flexion angle augmented by FES and exhibiting movement that more closely aligns with the neurotypical kinematic signal 1411b than with the neuro-atypical kinematic signal 1412a.

Additional Considerations

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm may be a sequence of operations leading to a desired result. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof. The operations are those requiring physical manipulations of physical quantities. Such quantities may take the form of electrical or magnetic signals capable of being stored, combined, compared, and otherwise manipulated. Such signals may be referred to as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the present disclosure, it is appreciated that throughout the description, certain terms refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may include a computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The algorithms and displays presented herein are not inherently related to any particular computer or other apparatus. Various other systems may be used with programs in accordance with the teachings herein, or it may prove convenient to construct a more specialized apparatus to perform the method. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments may also relate to a product that is produced by a computing process described herein. Such a product may comprise information resulting from a computing process, where the information is stored on a non-transitory, tangible computer readable storage medium and may include any embodiment of a computer program product or other data combination described herein.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment. Where values are described as "approximate" or "substantially" (or their derivatives), such values should be construed as accurate +/−10% unless another meaning is apparent from the context. From example, "approximately ten" should be understood to mean "in a range from nine to eleven."

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights, which is set forth in the following claims.

What is claimed is:

1. A method comprising:
   collecting a set of motor intent data of one or more users from a database;
   labeling the set of motor intent data with an intent label representative of intended motion characterized by the set of motor intent data;
   creating a training set based on the labeled set of motor intent data; and
   training a machine learning model using the training set, the machine learning model configured to output, based on monitored motor intent data, a movement prediction corresponding to likely motion characterized by the monitored motor intent data.

2. The method of claim 1, wherein the set of motor intent data comprises one or more of electromyography (EMG) data, inertial measurement unit (IMU) data, foot plantar pressure signals, or kinetic signals.

3. The method of claim 1, wherein the set of motor intent data comprises one or more of neurotypical motor intent data or neuro-atypical motor intent data.

4. The method of claim 1, further comprising determining the intent label based on one or more of foot plantar pressure signals, kinematic signals, and kinetic signals of one or more users from a database.

5. The method of claim 1, wherein the set of motor intent data is labeled by one or more of: the one or more users, one or more observers watching the one or more users, a computer vision algorithm configured to recognize motions within video, or a system configured to prompt the one or more users to perform particular actions.

6. The method of claim 1, wherein the set of motor intent data comprises one or both of: a plurality of motions performed by a plurality of users or a common motion performed by a plurality of users.

7. The method of claim 6, wherein the common motion is one of a step, a grasp, a lift, or a contraction.

8. The method of claim 1, wherein the machine learning model is further configured to output, based on monitored motor intent data, an actuation instruction corresponding to likely motion characterized by the monitored motor intent data.

9. The method of claim 8, wherein the actuation instruction includes a proportional steering ratio between electrical signals transmitted at electrodes of a wearable stimulation array.

10. The method of claim 8, further comprising:
    stimulating movement of a target user using the actuation instruction;
    determining a level of fatigue experienced by the target user during the stimulation; and
    adjusting the actuation instruction based on the level of fatigue.

11. The method of claim 10, wherein determining the level of fatigue comprises:
    measuring a first set of EMG signals of the target user during the stimulation;
    determining a frequency response of electroactivity in the first set of EMG signals; and
    comparing the frequency response to a baseline frequency response determined using a second set of EMG signals measured when the user was rested.

12. The method of claim 10, wherein determining the level of fatigue comprises:
    measuring the movement of the target user during the stimulation, the measured movement including one or more of foot plantar pressure signals, kinematic signals, and kinetic signals;
    tracking an amplitude of a signal of the measured movement; and
    comparing the tracked amplitude to a baseline signal profile of the movement.

13. The method of claim 8, further comprising:
    stimulating movement of a target user using the actuation instruction;

measuring the movement during the stimulation, the measured movement including one or more of foot plantar pressure signals, kinematic signals, and kinetic signals;

labeling the measured movement with the actuation instruction to generate another training set; and re-training the machine learning model using the labeled movement.

14. The method of claim 1, further comprising, for each user of the one or more users:

aligning the set of motor intent data of the respective user in a temporal domain;

processing the set of motor intent data of the respective user using one or more signal processing techniques selected from filtering, averaging, peak-finding, down-sampling, Fourier transforms, and a root mean square averaging; and determining kinematic data associated with the processed set of motor intent data of the respective user using a biomechanical model.

15. The method of claim 1, wherein the movement prediction corresponds to a movement template representative of a sequence of muscle firing events, the sequence of muscle firing events associated with a plurality of target movement signals.

16. The method of claim 1, wherein the movement prediction corresponding to the likely motion comprises a likely IMU data value at a subsequent time occurring after a time at which the monitored motor intent data is monitored.

17. The method of claim 1, wherein creating the training set based on the labeled set of motor intent data comprises determining a feature vector representative of muscle firing events located at different areas of a target user's body.

18. The method of claim 1, wherein the machine learning model is trained using one or more processors of a remote device.

19. A mobility improvement system comprising a non-transitory computer-readable storage medium storing instructions for execution and a hardware processor configured to execute the instructions, the instructions, when executed, cause the hardware processor to perform steps comprising:

collecting a set of motor intent data of one or more users from a database;

labeling the set of motor intent data with an intent label representative of intended motion characterized by the set of motor intent data;

creating a training set based on the labeled set of motor intent data; and training a machine learning model using the training set, the machine learning model configured to output, based on monitored motor intent data, a movement prediction corresponding to likely motion characterized by the monitored motor intent data.

20. A non-transitory computer readable storage medium storing executable instructions that, when executed by one or more processors, cause the one or more processors to perform steps comprising:

collecting a set of motor intent data of one or more users from a database;

labeling the set of motor intent data with an intent label representative of intended motion characterized by the set of motor intent data;

creating a training set based on the labeled set of motor intent data; and training a machine learning model using the training set, the machine learning model configured to output, based on monitored motor intent data, a movement prediction corresponding to likely motion characterized by the monitored motor intent data.

* * * * *